US009751886B2

(12) United States Patent
Oehlrich et al.

(10) Patent No.: US 9,751,886 B2
(45) Date of Patent: Sep. 5, 2017

(54) 4-AMINO-6-PHENYL-6,7-DIHYDRO[1,2,3]TRIAZOLO[1,5-A]PYRAZINE DERIVATIVES AS INHIBITORS OF BETA-SECRETASE (BACE)

(71) Applicant: Janssen Pharmaceutica NV, Beerse (BE)

(72) Inventors: Daniel Oehlrich, Brecht (BE); Henricus Jacobus Maria Gijsen, Breda (NL)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/897,396

(22) PCT Filed: Jun. 12, 2014

(86) PCT No.: PCT/EP2014/062286
§ 371 (c)(1),
(2) Date: Dec. 10, 2015

(87) PCT Pub. No.: WO2014/198854
PCT Pub. Date: Dec. 18, 2014

(65) Prior Publication Data
US 2016/0130274 A1    May 12, 2016

(30) Foreign Application Priority Data

Jun. 12, 2013  (EP) .................................... 13171720

(51) Int. Cl.
*C07D 487/04* (2006.01)
*A61K 31/4985* (2006.01)

(52) U.S. Cl.
CPC ........ *C07D 487/04* (2013.01); *A61K 31/4985* (2013.01)

(58) Field of Classification Search
None
See application file for complete search history.

(56) References Cited

U.S. PATENT DOCUMENTS

| 4,188,389 | A  | 2/1980  | Jirkovsky |
| 5,292,732 | A  | 3/1994  | Rover |
| 8,207,164 | B2 | 6/2012  | Holzer et al. |
| 2005/0282825 | A1 | 12/2005 | Malamas et al. |
| 2007/0005404 | A1 | 1/2007  | Raz et al. |
| 2007/0225372 | A1 | 9/2007  | Bueno Melendo et al. |
| 2008/0051420 | A1 | 2/2008  | Berg et al. |
| 2009/0082560 | A1 | 3/2009  | Kobayashi et al. |
| 2011/0009395 | A1 | 1/2011  | Audia et al. |
| 2012/0238557 | A1 | 9/2012  | Masui et al. |
| 2012/0277244 | A1 | 11/2012 | Tintelnot-Blomley et al. |
| 2016/0152581 | A1 | 6/2016  | Trabanco-Suarez et al. |

FOREIGN PATENT DOCUMENTS

| CA | 825620         | 9/2012  |
| EP | 2147914 A1     | 1/2010  |
| EP | 2518059        | 10/2012 |
| EP | 2147914 B1     | 6/2014  |
| JP | 2013-513563    | 4/2013  |
| JP | 2012-147763    | 7/2014  |
| JP | 2014-505688    | 3/2015  |
| WO | 9857641        | 12/1998 |
| WO | 03089434 A2    | 10/2003 |
| WO | WO03089434     | 10/2003 |
| WO | 2004026877 A1  | 4/2004  |
| WO | WO2004026877 A1| 4/2004  |
| WO | 2004058176 A2  | 7/2004  |
| WO | WO2005037832 A1| 4/2005  |
| WO | 2006034093 A2  | 3/2006  |
| WO | 2006076284 A2  | 7/2006  |
| WO | 2006138265 A2  | 12/2006 |
| WO | 2007005404 A1  | 1/2007  |
| WO | WO2006076284 A3| 4/2007  |
| WO | 2007058583 A2  | 5/2007  |
| WO | 2007114771 A1  | 10/2007 |
| WO | 2009022961 A1  | 2/2009  |

(Continued)

OTHER PUBLICATIONS

International Search Report—PCT/EP2011/059441.
International Search Report—PCT/EP2011/059330.
International Search Report—PCTEP2011/060712.
International Search Report—PCT/EP2011/066343.
International Search Report—PCT/EP2011/073522.
International Search Report—PCT/EP2012/053455.
International Search Report—PCT/EP2012/053863.
International Search Report—PCT/EP2012/074349.
International Search Report—PCT/EP2012/074351.
International Search Report—PCT/EP2014/062285.
International Search Report—PCT/EP2014/062286.
International Search Report—PCT/EP2014/062283.
Cheret et al., Bace1 and Neuregulin-1 cooperate to control formation and maintenance of muscle spindles, Bace1 and Neuregulin-1 cooperate to control formation and maintenance of muscle spindles, 2013, 2015-2028, 32(14), EMBO Journal.

(Continued)

*Primary Examiner* — Brian J Davis
(74) *Attorney, Agent, or Firm* — Yuriy P. Stercho

(57) ABSTRACT

The present invention relates to novel 6,7-dihydro[1,2,3]triazolo[1,5-a]pyrazin-6-yl derivatives as inhibitors of beta-secretase, also known as beta-site amyloid cleaving enzyme, BACE, in particular BACE1 and/or BACE2 (wherein BACE1, is also known as Asp2, or memapsin2 and BACE2 is also known as Asp1, Memapsin 1 or DRAP). The invention is also directed to pharmaceutical compositions comprising such compounds, to processes for preparing such compounds and compositions, and to the use of such compounds and compositions for the prevention and treatment of disorders in which beta-secretase is involved, such as Alzheimer's disease (AD), mild cognitive impairment, senility, dementia, dementia with Lewy bodies, Down's syndrome, dementia associated with stroke, dementia associated with Parkinson's disease, dementia of the Alzheimer's type, dementia associated with beta-amyloid, age-related macular degeneration, type 2 diabetes and other metabolic disorders.

13 Claims, No Drawings

(56) References Cited

FOREIGN PATENT DOCUMENTS

| WO | 2009058300 A1 | 5/2009 | | |
|---|---|---|---|---|
| WO | 2009097278 A1 | 8/2009 | | |
| WO | 2009102468 A1 | 8/2009 | | |
| WO | 2009134617 A1 | 11/2009 | | |
| WO | 2011002409 A1 | 1/2011 | | |
| WO | 2011009943 A1 | 1/2011 | | |
| WO | 2011020806 A1 | 2/2011 | | |
| WO | 2011071135 A1 | 6/2011 | | |
| WO | WO 2011/069934 | 6/2011 | | |
| WO | 2011080176 A1 | 7/2011 | | |
| WO | 2011154431 A1 | 12/2011 | | |
| WO | WO 2011/154374 | 12/2011 | | |
| WO | WO 2012/000933 | 1/2012 | | |
| WO | WO 2012/038438 | 3/2012 | | |
| WO | 2012085038 A1 | 6/2012 | | |
| WO | 2012098064 | 7/2012 | | |
| WO | WO 2012/095463 | 7/2012 | | |
| WO | 2012057247 A1 | 9/2012 | | |
| WO | 2012120023 A1 | 9/2012 | | |
| WO | WO 2012/117027 A1 * | 9/2012 | ........... | C07D 487/04 |
| WO | WO2012120023 A1 | 9/2012 | | |
| WO | WO 2012/147763 | 11/2012 | | |
| WO | 2013054291 | 4/2013 | | |
| WO | WO 2013/083556 | 6/2013 | | |
| WO | WO 2013/083557 | 6/2013 | | |
| WO | WO 2014-099794 | 6/2014 | | |
| WO | WO2004058176 | 7/2014 | | |
| WO | WO 2014/198851 | 12/2014 | | |
| WO | WO 2014/198853 | 12/2014 | | |
| WO | WO 2016-096979 | 6/2016 | | |

OTHER PUBLICATIONS

Esterhazy et al., Bace2 is a β Cell-Enriched Protease that Regulates Pancreatic β Cell Function and Mass, Cell Metabolism, 2011, pp. 365-377, 14.

Fleck, Bace 1 Dependent Neuregulin Processing, Alzheimer Res, 2012, 178-183, 9.

Ginman et al., Core Refinement toward permeable B-Secretase (BACE-1) Inhibitors, Journal of Medicinal chemistry, 2013, pp. 4181-4205, 56, 2013.

Hackam, et al., Translation of Research Evidence From animals to Humans, Translation of Research Evidence From animals to Humans, 2006, 1731-1732., 296(14), JAMA.

Haniu et al., Protein Structure and folding: Characterization of Alzheimer's β-secretase protein BACE: a Pepsin Family member with Unusual Properties, J. Biol. Chem, 2000, pp. 21099-21106, 275, J. Biol Chem.

Hemming et al., Identification of β-Secretase (BACE1) Substrates using Quantitative Proteomics, Identification of β-Secretase (BACE1) Substrates using Quantitative Proteomics, 2009, e8477, 4, PLS ONE.

Hilpert et al., B-Secretase (BACE1) Inhibitors with High in Vivo Efficacy Suitable for Clinical Evaluation in Alzheimer's Disease, Journal of Medicinal Chemistry, 2013, pp. 3980-3995, 56, 2013.

Hisashi Koike et al, Thimet Oligopeptidase Cleaves the Full-Length Alzheimer Amyloid Precursor Protein at a β-Secretase Cleavage Site in COS Cells, Journal of Biochemistry, Jul. 1, 1999, pp. 235-242, vol. 126 No. 1.

Hong et al, Structure of the Protease domain of memapsin 2(β-Secretase) Complexed with Inhibitor, Structure of the Protease domain of memapsin 2(β-Secretase) Complexed with Inhibitor, 2000, pp. 150-153, 290, Science.

J.G. Cannon, Burger's Medicinal Chemistry and Drug Discovery, ImmunoPharmaceutics, Inc., 1995, pp. 783-802, 784, Fifth Edition, vol. I, Wiley- Interscience.

Jonsson et al, A mutation in APP protects against Alzheimer's disease and age-related cognitive decline, A mutation in APP protects against Alzheimer's disease and age-related cognitive decline, 2012, pp. 96-99, 488, Nature.

Jordan, Tamoxifen: A Most Unlikely Pioneering Medicine, Nature Reviews, Mar. 2003, pp. 205-213, vol. 2.

Kim et al, Molecular Bases of Disease: Reduced Sodium Channel Nav1.1 Levels in BACE1-null Mice, Molecular Bases of Disease: Reduced Sodium Channel Nav1.1 Levels in BACE1-null Mice, 2011, 8106-8116, 286, J. Biol. Chem.

Kondoh et al, A novel aspartic protease gene, ALP56, is up-regulated in human breast cancer independently from the cathepsin D gene, A novel aspartic protease gene, ALP56, is up-regulated in human breast cancer independently from the cathepsin D gene, 2003, 37-44, 78, Breast Cancer Res.Treat.

Kuhn et al, Secretome protein enrichment identifies physiological BACE1protease substrates in neurons, Secretome protein enrichment identifies physiological BACE1protease substrates in neurons, 2012, 3157-3168, 31, EMBO J.

Kuhn et al2, Protein Synthesis, Post-translation Modification, and Degradation, Protein Synthesis, Post-translation Modification, and Degradation, 2007, pp. 11982-11995, vol. 282, No. 16, J. Biol. Chem.

Luo et al, Mice deficient in BACE!, the Alzheimer's (β-secretase, have normal phenotype and abolished β-amyloid generation, Mice deficient in BACE!, the Alzheimer's β-secretase, have normal phenotype and abolished β-amyloid generation, 2001, 231-232, 4, Nat. Neuroscience.

Naus et al, Enzyme Catalysis and Regulation, Enzyme Catalysis and Regulation, 2004, 16083-6090, 279, J.Biol. Chem.

Ostermann et al, Crystal Structure of Human BACE2 in Complex with a Hydroxyethylamine transition-state inhibito, Crystal Structure of Human BACE2 in Complex with a Hydroxyethylamine transition-state Inhibito, 2006, 249-61, 355, (2), Journal of molecular biology.

Park et al, Metabolism of Fluorine-Containing Drugs, Annual Review of Pharmacology and Toxicology, 2001, pp. 443-470, vol. 41.

Park, et al2, Effects of Flourine Substitution on Drug MetabolismPharmacological and Toxicological Implicatins:, Effects of Flourine Substitution on Drug Metabolism, 1994, pp. 605-643, vol. 26(3), Drug metabolism reviews.

Patani, et al., Bioisoterism: A Rational Approach in Drug Design, Chemical Reviews, 1996, pp. 3147-3176, vol. 96, No. 8.

Purser, et al, Flourine in Medicinal Chemistry, Flourine in Medicinal Chemistry, 2008, pp. 320-330, vol. 37, Chemical Society Reviews.

Roberds et al, BACE knockout mice are healthy despite lacking the primary β-secretase activity in the brain:, BACE knockout mice are healthy despite lacking the primary β-secretase activity in the brain:, 2001, 1317-1324, 10, Hum. Mol. Genet.

Robert P. Sheridan, The Most Common Chemical Replacements in Drug-Like Compounds, Journal of Chemical Information Comput. Sci., 2002, pp. 103-108, vol. 42 No. 1.

Rochin et al, BACE2 processes PMEL to form the melanosome amyloid matrix in pigment cells, BACE2 processes PMEL to form the melanosome amyloid matrix in pigment cells, Jun. 25 2013, pp. 10658-10663, vol. 110, No. 26, PNSA.

Silvestri et al, Boom in the Development of Non-Peptidic B-Secretase (BACE1) Inhibitors for the Treatment of Alzheimer's Disease, Medicinal Research Reviews, 2009, pp. 295-338, vol. 29, No. 2.

Stutzer et al, Systematic Proteomic Analysis Identifies β-Site Amyloid, 2013, 10536-10547, 288, J. Biol. Chem.

Vassar et al., Function, therapeutic potential and cell biology of BACE proteases: current status and future prospects, Function, therapeutic potential and cell biology of BACE proteases: current status and future prospects, 2014, 12715, 10.1111/jnc, J. Neurochem.

Vippagunta et al, Crystalline solids, Advanced Drug Delivery Reviews, May 16, 2001, pp. 3-26, vol. 48 No. 1.

Wang et al., β-Secretase: its biology as a therapeutic target in diseases, β-Secretase: its biology as a therapeutic target in diseases, 2013, pp. 215-225, vol. 34, No. 4, Trends in Pharmacological Sciences, Apr.

Willem et al, Function, regulation and therapeutic properties of β-secretase (BACE1), 2009, 175-182, 20, Semin. Cell Dev. Biol.

(56) References Cited

OTHER PUBLICATIONS

Woltering et al, BACE1 inhibitors: A head group scan on a series of amides, Bioorganic & Medicinal Chemistry Letters, 2013, pp. 4239-4243, 23, 2013.
Yan and Vassar, Targeting the β secretase BACE1 for Alzheimer's disease therapy, Targeting the β secretase BACE1 for Alzheimer's disease therapy, 2014, pp. 319-329, 13, Lancet Neurol.
Yan et al, Can BACE! Inhibition Mitigate Early Axonal Pathology in Neurological Diseases, Can BACE! Inhibition Mitigate Early Axonal Pathology in Neurological Disease, 2014, pp. 705-718, 30 vol. 38, No. 4, J Alzheimers Dis.
Zhou et al, The Neural Cell Adhesion Molecules L1and CHL1 are Cleaved by BACE1 Protease in Vivo, The Neural Cell Adhesion Molecules L1and CHL1 are Cleaved by BACE1 Protease in Vivo, 2012, 25927-25940, 287, J. Biol. Chem.
Wang et al., Chem. Rev, 2014, 114, 2432-2506.
Zhang, Foreign Medical Sciences (Geriatrics), Jan. 2008, vol. 29 No. 1, pp. 40-47 (translated article/reference from foreign Office Action, J&J File Ref. PRD3177CNPCT).
Martic-Kehl et al., Eur J. Nucl Med Mol Imaging (2012) 39: 1492-1496.
Mateu et al., Chem. Eur. J. 2015, 21, 11719-11726.
Oehlrich et al. The evolution of amidine-based brain penetrant BACE1 inhibitors_Bioorganic & Medicinal Chemistry Letters, 2014, vol. 24, pp. 2033-2045.

\* cited by examiner

4-AMINO-6-PHENYL-6,7-DIHYDRO [1,2,3]TRIAZOLO[1,5-A]PYRAZINE DERIVATIVES AS INHIBITORS OF BETA-SECRETASE (BACE)

CROSS REFERENCE TO RELATED APPLICATIONS

This application is the national stage of PCT Application No. PCT/EP2014/062286, filed Jun. 12, 2014, which claims priority from European Patent Application No. 13171720.9, filed Jun. 12, 2013, the entire disclosures of which are hereby incorporated in their entirety.

FIELD OF THE INVENTION

The present invention relates to novel 6,7dihydro[1,2,3]triazolo[1,5-a]pyrazin-6-yl derivatives as inhibitors of beta-secretase, also known as beta-site amyloid cleaving enzyme, BACE, in particular BACE1 and/or BACE2 (wherein BACE1, is also known as Asp2, or memapsin2 and BACE2 is also known as Asp1, Memapsin 1 or DRAP). The invention is also directed to pharmaceutical compositions comprising such compounds, to processes for preparing such compounds and compositions, and to the use of such compounds and compositions for the prevention and treatment of disorders in which beta-secretase is involved, such as Alzheimer's disease (AD), mild cognitive impairment, senility, dementia, dementia with Lewy bodies, Down's syndrome, dementia associated with stroke, dementia associated with Parkinson's disease, dementia of the Alzheimer's type, dementia associated with beta-amyloid. In addition to Alzheimer's disease, Down syndrome, and related diseases, BACE inhibition may find therapeutic and/or prophylactic treatment use in conditions such as traumatic brain injury (TBI), temporal lobe epilepsy (TLE), hypoxia, ischemia, cellular stress, neuroinflammatory disorders, disruptions in cerebral metabolism, age-related macular degeneration, Sjogren syndrome, Spinocerebellar ataxia 1, Spinocerebellar ataxia 7, Whippel's disease and Wilson's disease, age-related macular degeneration, amyotrophic lateral sclerosis (ALS), arterial thrombosis, autoimmune/inflammatory diseases, cardiovascular diseases such as myocardial infarction and stroke, dermatomyositis, gastrointestinal diseases, Glioblastoma multiforme, Graves' Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, type 2 diabetes and other metabolic disorders, malignant melanoma, multiple myeloma, and rheumatoid arthritis, hypertension, malignant melanoma and multiple melanoma and breast cancer.

BACKGROUND OF THE INVENTION

Alzheimer's disease (AD) is a neurodegenerative disease and the most common cause of dementia. Early memory problems and gradual and progressive decline in cognitive functions beyond normal ageing are characteristic for AD. Post-mortem studies have shown the neuropathological hallmarks of the disease include extracellular amyloid plaques mainly consisting of 38 to 43 amino acids long peptides called AP peptide and intracellular neurofibrillary tangles with hyperphosphorylated TAU protein as the characteristic component.

Aβ peptides are generated in the amyloidogenic pathway from the Amyloid Precursor Protein (APP). In this pathway, Aβ peptides are generated by the sequential action of two proteases, β- and γ-secretase. The β-secretase activity is exerted by the (3-site APP cleaving enzyme 1 (BACE1) and BACE1 mediated APP cleavage results in shedding of the extracellular APP ectodomain (sAPPβ). The remaining membrane-bound C-terminal fragment (C99) is further processed by γ-secretase, which catalyzes an unusual proteolysis within the transmembrane region, resulting in the release of the APP intracellular domain (AICD) in the cytosol and the exocytosis of Aβ peptides in the extracellular environment. The majority of Aβ produced is 40-amino acid residues in length (Aβ40). Although the 42-residue form (Aβ42) is a minor species, it more readily aggregates to produce fibrils and ultimately amyloid plaques.

Next to the pathology also human genetics studies strongly suggest that Aβ plays a central role in AD pathogenesis. Today, over 200 autosomal dominant mutations that cause familial AD (FAD) have been found in the genes for APP and presenilin, the active subunit of γ-secretase. These mutations invariably lead to either increased Aβ42 to Aβ40 ratio or over-production of total Aβ. Notably, the FAD mutations in APP are found near the β- and γ-secretase cleavage sites and make APP a more efficient substrate for endoproteolysis by the secretases. Of particular relevance here are the K670N; M671L (Swedish) double mutation and the A673V mutation that are adjacent to the β-secretase cleavage site and cause FAD by increasing β-secretase processing and total Aβ production. Interestingly genetic variants have been identified that protect against AD. A low-frequency mutation in APP, the A673T coding substitution, was recently shown to be associated with decreased risk of AD and reduced cognitive decline in the elderly (Jonsson et al. 2012, Nature 488, 96-99). APP harboring the A673T substitution—located two amino acids C-terminal to the β-secretase cleavage site is less efficiently cleaved by β-secretase, leading to a ~40% reduction in Aβ production in vitro.

Cleavage of APP by Beta-site APP Cleaving Enzyme1 (BACE1) is the rate limiting step in the generation of the Aβ peptide. BACE1 is a membrane-bound aspartyl protease that is optimally active at a slightly acidic pH. Although BACE1 is localized in various organelles, its activity is reported to be at a maximum in endosomes and to a lower extend in the trans golgi network (TGN), hence most APP is cleaved by BACE1 in the endocytic compartment. Evidence that BACE-1 is the sole β-secretase activity in the brain was provided by the observations that BACE-1 knockout mice completely lacked both β-secretase enzyme activity and the product of β-cleavage, CTF99 (Roberds et al., 2001, Hum. Mol. Genet. 10, 1317-1324, Luo et al., 2001, Nat. Neurosci. 4, 231-232). Ongoing clinical trials with BACE1 inhibitors confirm that BACE1 is the sole β-secretase activity in human brain, since pharmacological BACE1 inhibition blocks Aβ production.

Soon after the discovery of BACE1, a related membrane-bound aspartic protease BACE2 was identified that shares 64% amino acid similarity to BACE1. Although BACE2 can generate Aβ in vitro, it appears not to do so in vivo as mentioned above. BACE1 and its homologue BACE2 are members of the pepsin-like family of aspartic proteases (cathepsin D and E, pepsin A and C, renin, napsin A). They display a typical bilobal structure with the catalytic site located at the interface between the N- and the C-terminal lobe (Hong et al, 2000, Science 290, 150-153, Ostermann et al, 2006, Journal of molecular biology, 355, (2), 249-61). BACE1 and 2 are anchored to the cell membrane via a transmembrane domain, which, together with several unique amino acid stretches and the arrangement of the three disulfide bridges (Haniu et al., 2000, J. Biol. Chem. 275, 21099-21106) sets BACE apart from the rest of the pepsin family and facilitates the generation of relatively specific inhibitors for BACE1 and 2.

Next to APP a variety of CNS and peripheral BACE1 substrates and associated functions have been described (Hemming et al. 2009, PLoS ONE 4, e8477, Kuhn et al. 2012, EMBO J. 31, 3157-3168; Zhou et al. 2012, J. Biol. Chem. 287, 25927-25940, Stutzer et al. 2013, J. Biol. Chem. 288, 10536-10547, reviewed in Vassar et al., J. Neurochem. (2014) 10.1111/jnc.12715). Examples of BACE1 substrates are L1, CHL1, GLG1, PAM, SEZ6, SEZ6L, Jag1, NRG1, NaVβ2, VEGFR1 and APLP1. Consequently BACE1 has a wide variety of potential physiologic functions including, but not exclusively in cell differentiation, immunoregulation, myelination, synaptic development and plasticity, cell death, neurogenesis and axonal guidance (Wang et al. Trends in Pharmacological Sciences, April 2013, Vol 34, No. 4, pp. 215-225; Yan and Vassar Lancet Neurol. 2014, Vol. 13, pp. 319-329; Yan et al. J Alzheimers Dis. 2014, Vol. 38, No. 4, pp. 705-718).

For example in BACE1 knock-out mice, loss of cleavage of neuregulin 1 (NRG1) type III resulted in impaired post-natal myelination in the PNA and CNS (Fleck et al. 2012, Curr. Alzheimer Res. 9, 178-183; Willem et al. 2009, Semin. Cell Dev. Biol. 20, 175-182). Loss of cleavage of NRG1 type I results in abnormal muscle spindle formation and maintenance and associated defects in coordinated movement (Cheret et al. 2013). BACE1 processing of β-subunits of voltage-gated sodium channels controls cell-surface NaV channel density, neuronal excitability, and seizure susceptibility (Kim et al. 2011, J. Biol. Chem. 286, 8106-8116). BACE1-dependent CHL1 cleavage is known to be involved in axon outgrowth and neuronal survival (Naus et al. 2004, J. Biol. Chem. 279, 16083-16090). BACE1-dependent Jag1 cleavage regulates post-natal neurogenesis and astrogenesis by modulating Notch 1 signalling.

Therefore, in addition to Alzheimer's disease, Down syndrome, and related diseases, BACE inhibition may find therapeutic and/or prophylactic treatment use in conditions such as traumatic brain injury (TBI), temporal lobe epilepsy (TLE), hypoxia, ischemia, cellular stress, neuroinflammatory disorders, disruptions in cerebral metabolism, age-related macular degeneration, Sjogren syndrome, Spinocerebellar ataxia 1, Spinocerebellar ataxia 7, Whippel's disease and Wilson's disease, age-related macular degeneration, amyotrophic lateral sclerosis (ALS), arterial thrombosis, autoimmune/inflammatory diseases, cardiovascular diseases such as myocardial infarction and stroke, dermatomyositis, gastrointestinal diseases, Glioblastoma multiforme, Graves' Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple myeloma, and rheumatoid arthritis.

Also BACE2 has a broad expression profile, with relative high expression levels in most different cell types and organs in the periphery and lower level of expression in astrocytes in the brain. As mentioned above also BACE2 has a broad spectrum of substrates as exemplified by the study in the pancreatic islets mentioned above (Stutzer et al. 2013).

BACE2 is expressed in pancreatic 13 cells, where it cleaves Tmem27 (Esterházy et al. Cell Metabolism 2011). Inhibition of BACE2 therefore may provide a potential mechanism to result in increased β cell mass, and a potential mode of action in the treatment or prevention of Type2 diabetes BACE2 is also known to be involved in the cleavage of APP (Wang et al. Trends in Pharmacological Sciences, April 2013, Vol. 34, No. 4, pp. 215-225), IL-1R2 (Kuhn et al. J. Biol. Chem. 2007, Vol. 282, No. 16, pp. 11982-11995), and pigment cell-specific melanocyte protein (PMEL) (Rochin et al. PNAS, Jun. 25, 2013, Vol. 110, No. 26, pp. 10658-10663), therefore indicating a potential application for BACE2 inhibitors in the treatment of Down's syndrome, hypertension, malignant melanoma and multiple melanoma. BACE2 is unregulated in human breast cancers (Kondoh et al. Breast Cancer Res. Treat., 2003, Vol. 78, pp. 37-44), and therefore BACE2 inhibitors may provide a potential in the treatment of breast cancers.

Inhibitors of BACE1 and/or BACE2 may thus be useful for the therapeutic and/or prophylactic treatment of Alzheimer's disease (AD), mild cognitive impairment, senility, dementia, dementia with Lewy bodies, Down's syndrome, dementia associated with stroke, dementia associated with Parkinson's disease, dementia of the Alzheimer's type, dementia associated with beta-amyloid. In addition to Alzheimer's disease, and related diseases, BACE inhibition may find therapeutic and/or prophylactic treatment use in conditions such as traumatic brain injury (TBI), temporal lobe epilepsy (TLE), hypoxia, ischemia, cellular stress, neuroinflammatory disorders, disruptions in cerebral metabolism, age-related macular degeneration, Sjogren syndrome, Spinocerebellar ataxia 1, Spinocerebellar ataxia 7, Whippel's disease and Wilson's disease, age-related macular degeneration, amyotrophic lateral sclerosis (ALS), arterial thrombosis, autoimmune/inflammatory diseases, cardiovascular diseases such as myocardial infarction and stroke, dermatomyositis, gastrointestinal diseases, Glioblastoma multiforme, Graves' Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple myeloma, and rheumatoid arthritis, type 2 diabetes and other metabolic disorders, hypertension, malignant melanoma and multiple melanoma and breast cancer.

WO 2012/117027 (Janssen Pharmaceutica NV) discloses 4-amino-6-phenyl-6,7-dihydropyrazolo[1,5-a]pyrazine derivatives as BACE inhibitors. WO 2012/057247 (Shionogi & Co., Ltd.) describes fused aminodihydropyrimidine derivatives useful as BACE inhibitors.

SUMMARY OF THE INVENTION

It is the object of the present invention to provide compounds with BACE inhibitory activity. The present invention is directed to 6,7-dihydro[1,2,3]triazolo[1,5-a]pyrazin-6-yl derivatives of Formula (I)

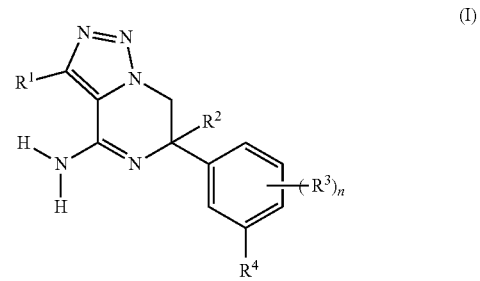

and the stereoisomeric forms thereof, wherein
$R^1$ is selected from the group of hydrogen; halo; and $C_{1-4}$alkyl;
$R^2$ is selected from the group of $C_{1-4}$alkyl optionally substituted with one or more substituents each independently selected from fluoro and $C_{1-4}$alkyloxy; and $C_{3-7}$ cycloalkyl;
$R^3$ is in each instance an independently selected halo substituent;
n is an integer selected from 1 and 2;
$R^4$ is selected from (a) and (b):

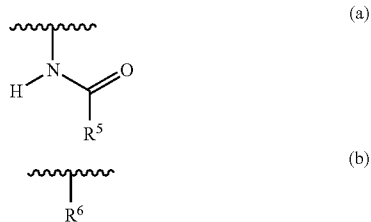

wherein $R^5$ and $R^6$ are each independently selected from the group of aryl and heteroaryl, each of which may be optionally substituted with one or more substituents each independently selected from the group of halo, —CN, $C_{1-4}$alkyl optionally substituted with one or more halo substituents, and $C_{1-4}$alkyloxy optionally substituted with one or more halo substituents;
wherein aryl is phenyl;
wherein heteroaryl is a 5-membered aromatic heterocycle selected from the group consisting of oxazole and pyrazole; or is a 6-membered aromatic heterocycle selected from the group consisting of pyridinyl, pyrimidinyl and pyrazinyl;
and the pharmaceutically acceptable addition salts and the solvates thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by the beta-secretase enzyme, comprising administering to a subject in need thereof a therapeutically effective amount of any of the compounds or pharmaceutical compositions described herein.

Further exemplifying the invention are methods of inhibiting the beta-secretase enzyme, comprising administering to a subject in need thereof a therapeutically effective amount of any of the compounds or pharmaceutical compositions described herein.

An example of the invention is a method of treating or preventing a disorder selected from the group consisting of Alzheimer's Disease (AD), mild cognitive impairment (MCI), memory impairment, senility, dementia, dementia with Lewy bodies, dementia with progressive nuclear palsy, dementia with Cortico-basal degeneration, mixed dementia with Alzheimer's and vascular type, Alzheimer's disorder with difuse Lewy Body disease, amyloid angiopathy, cerebral amyloid angiopathy, multi-infarct dementia, Down's syndrome, dementia associated with Parkinson's disease, dementia of the Alzheimer's type, senile dementia of the Alzheimer's type, vascular dementia, dementia due to HIV disease, dementia due to head trauma, dementia due to Huntington's disease, dementia due to Pick's disease, dementia due to Creutzfeldt-Jakob disease, frontotemporal dementia, dementia pugilistica, dementia associated with beta-amyloid, amyloidosis of the brain and other organs (age and non-age related), Dutch type of hereditary cerebral haemorrhage with amyloidosis, traumatic brain injury (TBI), temporal lobe epilepsy (TLE), hypoxia, ischemia, disruptions in cerebral metabolism, age-related macular degeneration, type 2 diabetes and other metabolic disorders, amyotrophic lateral sclerosis (ALS), multiple sclerosis (MS), arterial thrombosis, autoimmune/inflammatory diseases, cancer such as breast cancer, cardiovascular diseases such as myocardial infarction and stroke, hypertension, dermatomyositis, prion disease (Creutzfeld-Jakob disease), gastrointestinal diseases, Glioblastoma multiforme, Graves' Disease, Huntington's Disease, inclusion body myositis (IBM), inflammatory reactions, Kaposi Sarcoma, Kostmann Disease, lupus erythematosus, macrophagic myofasctitis, juvenile idiopathic arthritis, granulomatous arthritis, malignant melanoma, multiple myeloma, rheumatoid arthritis, Sjogren syndrome, SpinoCerebellar Ataxia 1, SpinoCerebellar Ataxia 7, Whippel's Disease and Wilson's Disease. An additional example of the invention is a method of treating a disorder selected from the group consisting of Alzheimer's disease, mild cognitive impairment, senility, dementia, dementia with Lewy bodies, cerebral amyloid angiopathy, multi-infarct dementia, Down's syndrome, dementia associated with stroke, dementia associated with Parkinson's disease, dementia of the Alzheimer's type and dementia associated with beta-amyloid, preferably Alzheimer's disease, comprising administering to a subject in need thereof, a therapeutically effective amount of any of the compounds or pharmaceutical compositions described herein.

A further example of the invention is a method of treating a neurocognitive disorder (NCD) selected from a neurocognitive disorder due to Alzheimer's disease, due to traumatic brain injury (TBI), due to Lewy body disease, due to Parkinson's disease or to vascular NCD (such as vascular NCD present with multiple infarctions), comprising administering to a subject in need thereof, a therapeutically effective amount of any of the compounds or pharmaceutical compositions described herein.

Another example of the invention is any of the compounds described above for use in treating: (a) Alzheimer's Disease, (b) mild cognitive impairment, (c) senility, (d) dementia, (e) dementia with Lewy bodies, (f) Down's syndrome, (g) dementia associated with stroke, (h) dementia associated with Parkinson's disease, (i) dementia of the Alzheimer's type, (j) dementia associated with beta-amyloid, (k) age-related macular degeneration, (k) type 2 diabetes and (l) other metabolic disorders, in a subject in need thereof

DETAILED DESCRIPTION OF THE INVENTION

The present invention is directed to compounds of Formula (I) as defined hereinbefore and pharmaceutically acceptable salts and solvates thereof. The compounds of Formula (I) are inhibitors of the beta-secretase enzyme (also known as beta-site cleaving enzyme, BACE, in particular BACE1 (also known as Asp2 or memapsin 2), and/or BACE2 (also known as Asp1, Memapsin 1 or DRAP)), and may be useful in the treatment or prevention of Alzheimer's disease, mild cognitive impairment, senility, dementia, dementia associated with stroke, dementia with Lewy bodies, Down's syndrome, dementia associated with Parkinson's disease, dementia of the Alzheimer's type, dementia associated with beta-amyloid, age-related macular degeneration, type 2 diabetes and other metabolic disorders, preferably Alzheimer's disease, mild cognitive impairment or dementia, type 2 diabetes and other metabolic disorders, more preferably Alzheimer's disease and/or type 2 diabetes. Furthermore, the compounds of Formula (I) may be useful in the treatment of neurocognitive disorder due to Alzheimer's disease, due to traumatic brain injury (TBI), due to Lewy body disease, due to Parkinson's disease or to vascular NCD (such as vascular NCD present with multiple infarctions). In particular, the compounds of Formula (I) may be useful in the treatment of Alzheimer's disease, mild cognitive impairment, senility, dementia, dementia associated with stroke, dementia with Lewy bodies, Down's syndrome, dementia associated with Parkinson's disease, dementia of the Alzheimer's type and dementia associated with beta-amyloid, preferably Alzheimer's disease, mild cognitive impairment or dementia, more preferably Alzheimer's disease. Furthermore, the compounds of Formula (I) may be useful in the treatment of neurocognitive disorder due to Alzheimer's disease, due to traumatic brain injury (TBI), due to Lewy body disease, due to Parkinson's disease or to vascular NCD (such as vascular NCD present with multiple infarctions). In particular, the compounds of Formula (I) may be useful in the treatment or prevention of Alzheimer's disease (or dementia of the Alzheimer's type, or neurocognitive disorder due to Alzheimer's disease). In particular, the compounds of Formula (I) may be useful in the treatment or prevention of type 2 diabetes.

In an embodiment, the present invention relates to compounds of Formula (I) as defined hereinabove, and stereoisomeric forms thereof, wherein $R^1$ is selected from the group of hydrogen; halo; and $C_{1-4}$alkyl;

$R^2$ is $C_{1-4}$alkyl optionally substituted with one or more substituents each independently selected from fluoro, and $C_{1-4}$alkyloxy;

$R^3$ is in each instance an independently selected halo substituent;

n is an integer selected from 1 and 2;

$R^4$ is

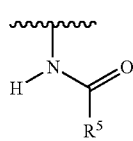

(a)

wherein $R^5$ is selected from the group of aryl and heteroaryl, each of which may be optionally substituted with one or more substituents each independently selected from the group of halo, —CN, $C_{1-4}$alkyl optionally substituted with one or more halo substituents, and $C_{1-4}$alkyloxy optionally substituted with one or more halo substituents; wherein aryl is phenyl;

wherein heteroaryl is a 5-membered aromatic heterocycle selected from the group consisting of oxazole and pyrazole; or is a 6-membered aromatic heterocycle selected from the group consisting of pyridinyl, pyrimidinyl and pyrazinyl; and the pharmaceutically acceptable salts and the solvates thereof.

In an embodiment of the invention, $R^1$ is hydrogen or halo, in particular hydrogen, and the rest of the variables are as defined in Formula (I) herein.

In an embodiment of the invention, $R^2$ is $C_{1-4}$alkyl optionally substituted with one or more halo substituents, in particular fluoro substituents, and the rest of the variables are as defined in Formula (I) herein.

In an embodiment of the invention, $R^2$ is $C_{1-4}$alkyl and the rest of the variables are as defined in Formula (I) herein.

In another embodiment of the invention, $R^4$ is

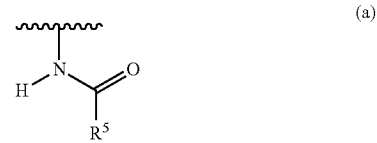

(a)

wherein $R^5$ is heteroaryl, optionally substituted with one or more substituents each independently selected from the group of halo, —CN, $C_{1-4}$alkyl optionally substituted with one or more halo substituents, and $C_{1-4}$alkyloxy optionally substituted with one or more halo substituents;

wherein heteroaryl is a 5-membered aromatic heterocycle selected from oxazole and pyrazole; or is a 6-membered aromatic heterocycle selected from the group consisting of pyridinyl, pyrimidinyl and pyrazinyl;

and the rest of variables are as defined in Formula (I) herein.

In another embodiment, the present invention relates to compounds of Formula (I) as defined hereinabove, and stereoisomeric forms thereof, wherein $R^1$ is hydrogen;

$R^2$ is $C_{1-4}$alkyl optionally substituted with one or more halo substituents, in particular, fluoro substituents, more in particular 1-3 fluoro substituents;

$R^3$ is halo, in particular fluoro; and n is 1 or 2;

$R^4$ is

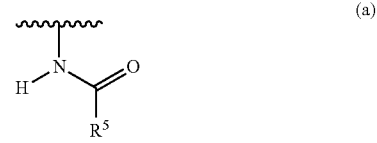

(a)

wherein $R^5$ is pyrazole, pyridinyl, pyrimidinyl or pyrazinyl, each of which may be optionally substituted with one or two substituents each independently selected from the group of halo, —CN, $C_{1-4}$alkyl optionally substituted with 1-3 halo substituents, in particular fluoro, and $C_{1-4}$alkyloxy optionally substituted with 1-3 halo substituents; and the pharmaceutically acceptable salts and the solvates thereof.

In another embodiment, the present invention relates to compounds of Formula (I) as defined hereinabove, and stereoisomeric forms thereof, wherein $R^1$ is hydrogen;

$R^2$ is $C_{1-4}$alkyl;

$R^3$ is halo, in particular fluoro; and n is 1;

$R^4$ is

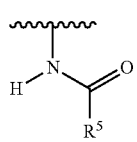

(a)

wherein $R^5$ is pyrazole, pyridinyl, pyrimidinyl or pyrazinyl, each of which may be optionally substituted with one or two substituents each independently selected from the group of halo, —CN, and $C_{1-4}$alkyloxy optionally substituted with one or more halo substituents;
and the pharmaceutically acceptable salts and the solvates thereof In a further embodiment, the present invention relates to compounds of Formula (I) as defined hereinabove, and stereoisomeric forms thereof, wherein
$R^1$ is hydrogen;
$R^2$ is $C_{1-4}$alkyl;
$R^3$ is halo, in particular fluoro; and n is 1;
$R^4$ is

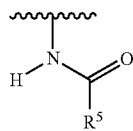

(a)

wherein $R^5$ is pyrazole, pyridinyl, pyrimidinyl or pyrazinyl, each of which may be optionally substituted with one or two substituents each independently selected from the group of halo, —CN, and $C_{1-4}$alkyloxy optionally substituted with one or more fluoro substituents;
and the pharmaceutically acceptable salts and the solvates thereof.

In another embodiment, the present invention relates to compounds of Formula (I) as defined hereinabove, and stereoisomeric forms thereof, wherein
$R^1$ is hydrogen;
$R^2$ is $C_{1-4}$alkyl;
$R^3$ is halo, in particular fluoro; and n is 1;
$R^4$ is

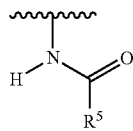

(a)

wherein $R^5$ is pyridinyl, pyrimidinyl or pyrazinyl, each of which may be optionally substituted with one or two substituents each independently selected from the group of halo, —CN, and $C_{1-4}$alkyloxy;
and the pharmaceutically acceptable salts and the solvates thereof.
In a yet further embodiment, the present invention relates to compounds of Formula (I) as defined hereinbefore wherein the quaternary carbon atom substituted with $R^2$ has a configuration as depicted in the structure (I') below wherein the 5,6-dihydroimidazo[1,5-a]pyrazin-3(2H)-one core is in the plane of the drawing, $R^2$ is projected below the plane of the drawing (with the bond shown with a wedge of parallel lines ⫴⫴⫴) and Ar is projected above the plane of the drawing (with the bond shown with a bold wedge ◢).

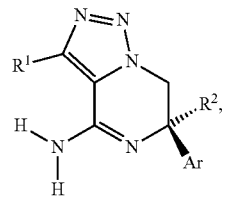

(I')

wherein Ar is

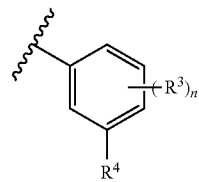

in particular Ar is

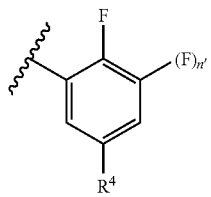

In an additional embodiment, the present invention relates to compounds of Formula (I) as defined hereinabove having the structure (I'a)

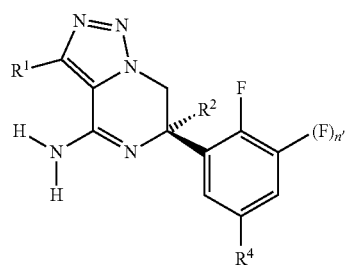

(Ia')

and stereoisomeric forms thereof, wherein
$R^1$ is hydrogen;
$R^2$ is $C_{1-4}$alkyl optionally substituted with one or more halo substituents, in particular, fluoro substituents, more in particular 1-3 fluoro substituents;
n' is 0 or 1;

$R^4$ is

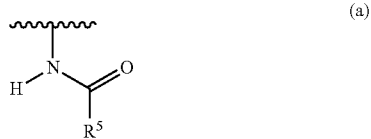

wherein $R^5$ is pyrazole, pyridinyl, pyrimidinyl or pyrazinyl, each of which may be optionally substituted with one or two substituents each independently selected from the group of halo, —CN, $C_{1-4}$alkyl optionally substituted with 1-3 halo substituents, in particular fluoro, and $C_{1-4}$alkyloxy optionally substituted with 1-3 halo substituents; and the pharmaceutically acceptable salts and the solvates thereof Specific compounds according to the invention include:

N-{3-[(6R)-4-Amino-6-methyl-6,7-dihydro[1,2,3]triazolo[1,5-a]pyrazin-6-yl]-4-fluorophenyl}-5-methoxypyrazine-2-carboxamide;

N-{3-[(6R)-4-Amino-6-methyl-6,7-dihydro[1,2,3]triazolo[1,5-a]pyrazin-6-yl]-4-fluorophenyl}-5-cyanopyridine-2-carboxamide;

N-{3-[(6R)-4-amino-6-methyl-6,7-dihydro[1,2,3]triazolo[1,5-a]pyrazin-6-yl]-4-fluorophenyl}-5-fluoropyridine-2-carboxamide; and N-{3-[6R)-4-amino-6-methyl-6,7-dihydro[1,2,3]triazolo[1,5-a]pyrazin-6-yl]-4-fluoropheny}-5-chloropyridine-2-carboxamide;

N-{3-[(6R)-4-amino-6-methyl-6,7-dihydro[1,2,3]triazolo[1,5-a]pyrazin-6-yl]-4-fluoropheny}-5-(2,2,2-trifluoroethoxy)pyrazine-2-carboxamide;

N-{3-[(6R)-4-amino-6-methyl-6,7-dihydro[1,2,3]triazolo[1,5-a]pyrazin-6-yl]-4-fluorophenyl}-4-chloro-1-(difluoromethyl)-1H-pyrazole-3-carboxamide;

N-{3-[(6R)-4-amino-6-methyl-6,7-dihydro[1,2,3]triazolo[1,5-a]pyrazin-6-yl]-4-fluoropheny}-5-(fluoromethoxy)pyrazine-2-carboxamide;

(rac)-N-{3-[4-amino-6-(fluoromethyl)-6,7-dihydro[1,2,3]triazolo[1,5-a]pyrazin-6-yl]-4-fluorophenyl}-5-fluoropyridine-2-carboxamide;

N-{3-[(6S)-4-amino-6-(fluoromethyl)-6,7-dihydro[1,2,3]triazolo[1,5-a]pyrazin-6-yl]-4-fluorophenyl}-5-fluoropyridine-2-carboxamide;

N-{3-[(6R)-4-amino-6-(fluoromethyl)-6,7-dihydro[1,2,3]triazolo[1,5-a]pyrazin-6-yl]-4-fluorophenyl}-5-fluoropyridine-2-carboxamide; and N-{3-[(6R)-4-amino-6-methyl-6,7-dihydro[1,2,3]triazolo[1,5-a]pyrazin-6-yl]-4,5-difluorophenyl}-5-fluoropyridine-2-carboxamide;

and the pharmaceutically acceptable salts and solvates of such compounds.

DEFINITIONS

"$C_{1-4}$alkyl" as used herein alone or as part of another group, defines a saturated, straight or branched, hydrocarbon radical having, 1, 2, 3 or 4 carbon atoms, such as methyl, ethyl, 1-propyl, 1-methyl, butyl, 1-methyl-propyl, 2-methyl-1-propyl, 1,1-dimethylethyl and the like. "$C_{1-4}$alkyloxy" shall denote an ether radical wherein $C_{1-4}$alkyl is as defined herein. "Halo" shall denote fluoro, chloro and bromo. "$C_{3-7}$cycloalkyl" shall denote cyclopropyl, cyclobutyl, cyclopentyl, cyclohexyl and cycloheptyl.

Whenever the term "substituted" is used in the present invention, it is meant, unless otherwise indicated or is clear from the context, to indicate that one or more hydrogens, preferably from 1 to 3 hydrogens, or from 1 to 2 hydrogens, or 1 hydrogen, on the atom or radical indicated in the expression using "substituted" is replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Hereinbefore and hereinafter, the term "compound of formula (I)" is meant to include the addition salts, the solvates and the stereoisomers thereof.

The terms "stereoisomers" or "stereochemically isomeric forms" hereinbefore or hereinafter are used interchangeably.

The invention includes all stereoisomers of the compound of Formula (I) either as a pure stereoisomer or as a mixture of two or more stereoisomers.

Enantiomers are stereoisomers that are non-superimposable minor images of each other. A 1:1 mixture of a pair of enantiomers is a racemate or racemic mixture. Diastereomers (or diastereoisomers) are stereoisomers that are not enantiomers, i.e. they are not related as minor images. Therefore, the invention includes enantiomers, diastereomers, racemates.

The absolute configuration is specified according to the Cahn-Ingold-Prelog system. The configuration at an asymmetric atom is specified by either R or S. Resolved compounds whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of formula (I) is for instance specified as (R), this means that the compound is substantially free of the (S) isomer.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Representative acids which may be used in the preparation of pharmaceutically acceptable salts include, but are not limited to, the following: acetic acid, 2,2-dichloro-acetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, capric acid, caproic acid, caprylic acid, cinnamic acid, citric acid, cyclamic acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, beta-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, trifluoromethylsulfonic acid, and undecylenic acid. Representative bases which may be used in the preparation of pharmaceutically acceptable salts include, but are not limited to, the following: ammonia, L-arginine, benethamine, benzathine, calcium hydroxide, choline, dimethylethanolamine, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The names of the compounds of the present invention were generated according to the nomenclature rules agreed upon by the Chemical Abstracts Service (CAS) using Advanced Chemical Development, Inc., software (ACD/Name product version 10.01; Build 15494, 1 Dec. 2006 or ACD/ChemSketch product version 12.5; Build 47877, 20 Apr. 2011) or according to the nomenclature rules agreed upon by the International Union of Pure and Applied Chemistry (IUPAC) using Advanced Chemical Development, Inc., software (ACD/Name product version 10.01.0.14105, October 2006). In case of tautomeric forms, the name of the depicted tautomeric form of the structure was generated. The other non-depicted tautomeric form is also included within the scope of the present invention.

Preparation of the Compounds

A. Preparation of the Final Compounds

Experimental Procedure 1

Final compounds according to Formula (I) wherein $R^4$ is —NHCOR$^5$, hereby named (I-a), can be prepared by reacting an intermediate compound of Formula (II-a) with an intermediate of Formula (III) (Reaction Scheme 1). That reaction can be performed in a suitable solvent, such as methanol (MeOH), in the presence of a condensation agent, such as 1-(3-dimethylaminopropyl)-3-ethylcarbodiimide hydrochloride or 4-(4,6-dimethoxy-1,3,5-triazin-2-yl)-4-methylmorpholinium chloride under suitable reaction conditions, such as at a convenient temperature, typically rt, for a period of time to ensure the completion of the reaction. An intermediate compound of Formula (III) can be obtained commercially or synthesized according to literature procedures. In Reaction Scheme 1, all variables are defined as in Formula (I).

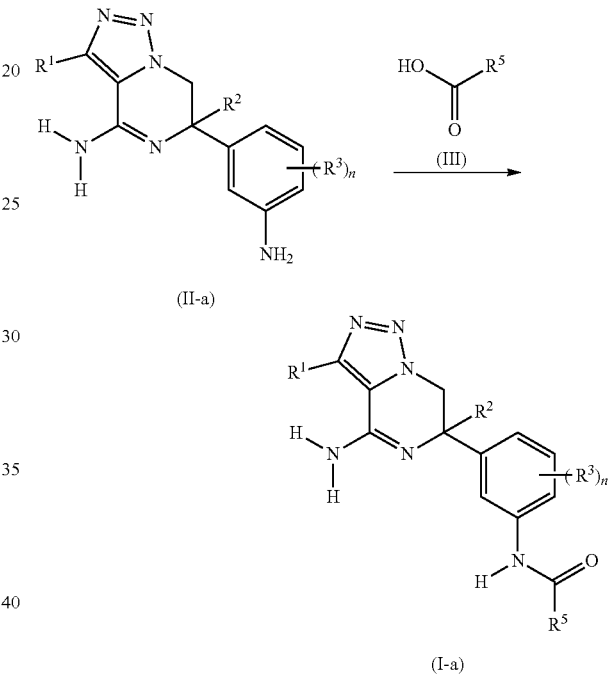

Experimental Procedure 2

Alternatively final compounds according to Formula (I) wherein $R^4$ is —$R^6$, hereby named (I-b), can be prepared by reacting an intermediate compound of Formula (IV-a) with an intermediate of Formula (V-a) (Reaction Scheme 2). The reaction can be performed in a suitable solvent, such as, 1,4-dioxane, in the presence of a suitable base, such as, sodium carbonate ($Na_2CO_3$), in the presence of a Pd-complex catalyst such as, 1,1'-bis(diphenylphosphino)ferrocene-palladium(II) dichloride dichloromethane complex, under suitable reaction conditions, such as at a convenient temperature, typically 100° C., for a period of time to ensure the completion of the reaction. An intermediate compound of Formula (V-a) can be obtained commercially or synthesized according to literature procedures. In Reaction Scheme 2, X is halo, $R^a$ and $R^b$ may be hydrogen or $C_{1-4}$alkyl, or may be taken together to form, for example a bivalent radical of formula —$CH_2CH_2$—, —$CH_2CH_2CH_2$—, or —$C(CH_3)_2C(CH_3)_2$— and all other variables are defined as in Formula (I).

Reaction Scheme 2

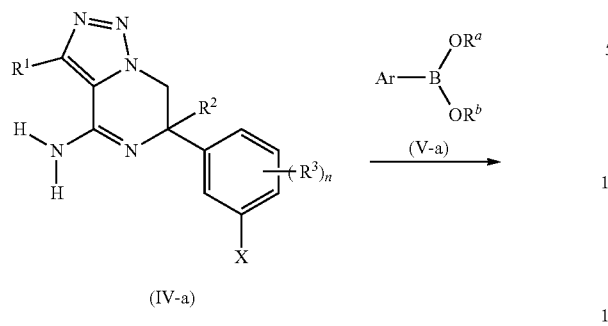

(IV-a)

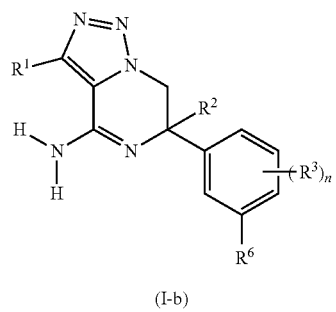

(I-b)

B. Preparation of the Intermediate Compounds

Experimental Procedure 3a

Intermediate compounds of Formula (II-a) can be prepared by a copper-catalyzed coupling reaction of an intermediate compound of Formula (IV-a) with sodium azide in the presence of a copper catalyst, such as copper(I) iodide, in the presence of a suitable ligand, such as, N,N'-dimethylethylenediamine, in the presence of a suitable base, such as $Na_2CO_3$ and in a suitable solvent, such as dimethylsulfoxide (DMSO). Degassing the reaction mixture with an inert gas, such as $N_2$ or argon, and heating the reaction mixture to high temperatures, such as at about 110° C., may enhance the reaction outcome. In Reaction Scheme 3a, X is halo and all other variables are defined as in Formula (I).

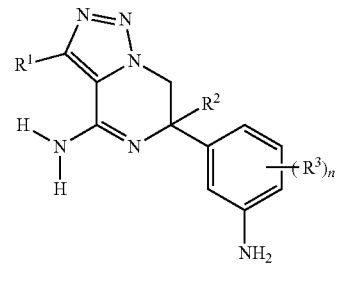

(II-a)

Experimental Procedure 3b

The intermediates according to Formula (II-b) can be prepared from the corresponding intermediate of Formula (IV-a) following art-known Buchwald-Hartwig type coupling procedures between an intermediate of formula (IV-a) and (V-b) to give an intermediate of Formula (II-b), followed by hydrolysis of (II-b) to give (II-a) according to Reaction Scheme 3b. Said Buchwald-Hartwig coupling may be conducted by treatment of intermediate compounds of Formula (IV-a) with an intermediate of Formula (V-b) in a suitable reaction-inert solvent, such as, for example, toluene, in the presence of a suitable base, such as, for example, sodium tert-butoxide, a Pd-complex catalyst such as, for example, tris(dibenzylideneacetone)dipalladium(0) [$Pd_2(dba)_3$, CAS 51364-51-3], a phosphine-ligand such as, for example, racemic-2,2'-bis(diphenylphosphino)-1,1'-binaphthyl [rac-BINAP, CAS 98327-87-8] under thermal conditions such as, for example, heating the reaction mixture at 90° C., for example for 18 hours. The hydrolysis of (II-b) to (II-a) can be carried out under acidic conditions, for example by treatment with HCl in 2-propanol at room temperature for 1-4 hours. In Reaction Scheme 3b, X is halo and all other variables are defined as in Formula (I).

Reaction Scheme 3a

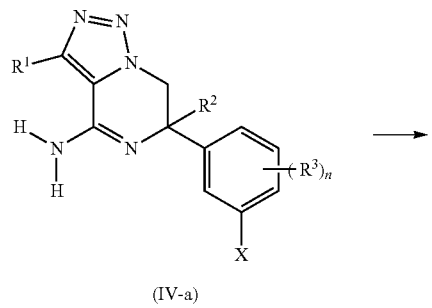

(IV-a)

Reaction Scheme 3b

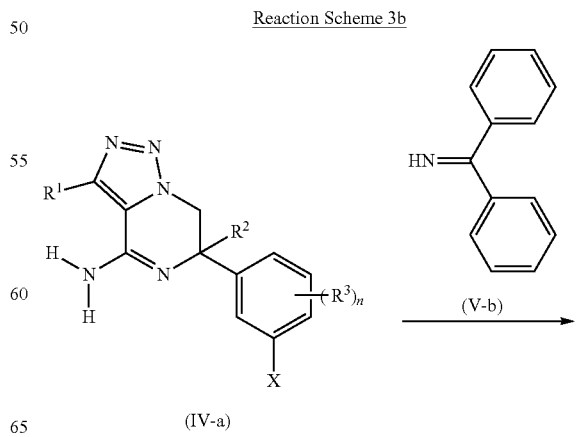

(IV-a)     (V-b)

-continued

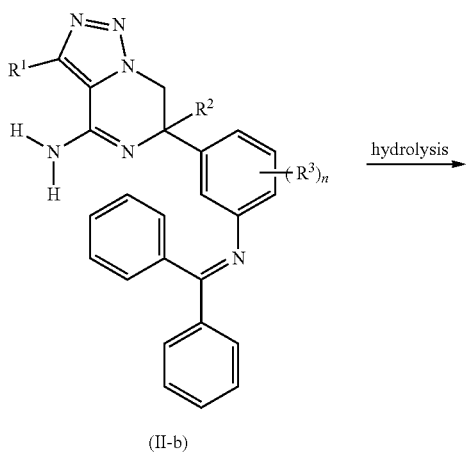

(II-b)

↓ hydrolysis (II-a)

Experimental Procedure 3c

Additionally, the intermediates according to Formula (II-a) can be prepared from the corresponding intermediates of Formula (II-c) following art-known nitro-to-amino reduction procedures according to Reaction Scheme 3c. Said reduction may conveniently be conducted by treatment of the corresponding intermediate of Formula (II-c) with iron metal in the presence of a suitable additive salts such as ammonium chloride in a suitable solvent, such as, MeOH/water, under suitable reaction conditions, such as at a convenient temperature, typically 70° C. for a period of time to ensure the completion of the reaction. Alternatively, reduction may be conveniently conducted following catalytic hydrogenation procedures. For example, said reduction may be carried out by stirring the reactants under a hydrogen atmosphere and in the presence of an appropriate catalyst such as, for example, palladium-on-charcoal, platinum-on-charcoal, Raney-nickel and the like catalysts. Suitable solvents are, for example, water, alkanols, e.g. methanol, ethanol and the like, esters, e.g. ethyl acetate and the like. In order to enhance the rate of said reduction reaction it may be advantageous to elevate the temperature and/or the pressure of the reaction mixture. Undesired further hydrogenation of certain functional groups in the reactants and the reaction products may be prevented by the addition of a catalyst poison such as, for example, thiophene and the like, to the reaction mixture.

Intermediate compounds of Formula (II-c) can be prepared from the corresponding intermediates of Formula (IV-b) following art-known nitration procedures according to Reaction Scheme 3c. Said nitration may conveniently be conducted by treatment of the corresponding intermediate compounds of Formula (IV-b) with a nitrating agent such as, for example, fuming nitric acid at low temperature such as, for example, 0° C., for example, for 30 minutes.

In Reaction Scheme 3c, all variables are defined as in Formula (I).

Reaction Scheme 3c

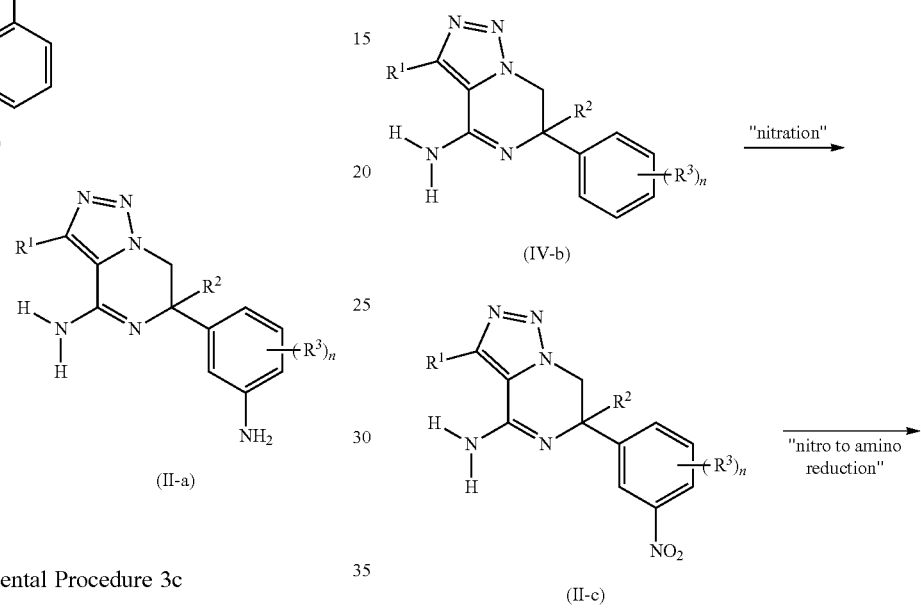

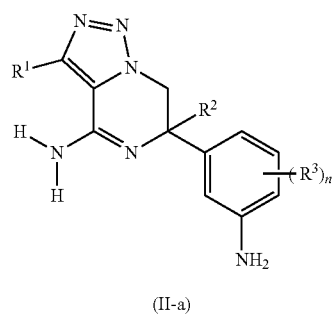

(II-a)

Experimental Procedure 4

Intermediate compounds of Formula (IV-c) wherein Z is hydrogen or halo, can be prepared by reacting an intermediate compound of Formula (VI) with an appropriate source of ammonia such as, for example, a solution of ammonia in MeOH (Reaction Scheme 4). That reaction can be performed in a suitable reaction-inert solvent, such as, MeOH, under suitable reaction conditions, such as at a convenient temperature, typically ranging between 50° C. and 90° C., for a period of time to ensure the completion of the reaction. In Reaction Scheme 4, Z is hydrogen or halo and all other variables are defined as in Formula (I).

Reaction Scheme 4

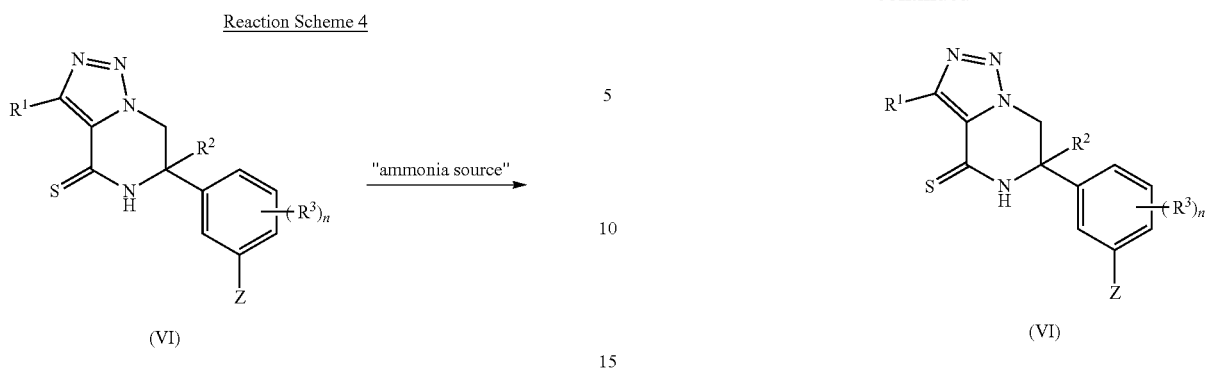

(VI) → "ammonia source" → (VI)

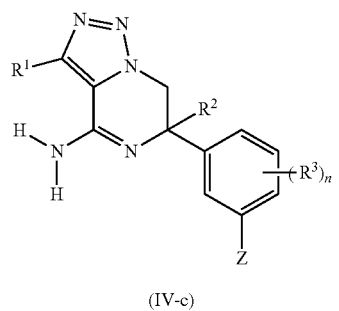

(IV-c)

Experimental Procedure 5

Intermediate compounds of Formula (VI) wherein Z is hydrogen or halo, can be prepared by reacting an intermediate compound of Formula (VII-a) with a suitable sulphur donating reagent for the synthesis of thioamides such as, for example, phosphorous pentasulfide. That reaction can be performed in a reaction inert solvent, such as for example, tetrahydrofuran, under suitable reaction conditions, such as at a convenient temperature, typically ranging between 50° C. and 90° C., for a period of time to ensure the completion of the reaction. In Reaction Scheme 5, Z is hydrogen or halo and all other variables are defined as in Formula (I).

Reaction Scheme 5

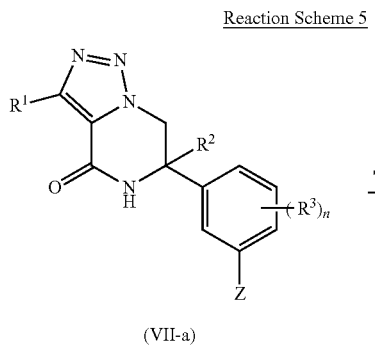

(VII-a) → "thionation" →

Experimental Procedure 6a

Intermediate compounds of Formula (VII-b) can be prepared from an intermediate compound of Formula (VIII-a) following art-known cyclization procedures. Said cyclization may conveniently be conducted by heating of an intermediate compound of Formula (VIII-a) in a suitable reaction solvent, such as N,N-dimethylformamide (DMF), under suitable reaction conditions, such as at a convenient temperature, typically ranging between 80° C. and 120° C., for a period of time to ensure the completion of the reaction.

Intermediate compounds of Formula (VIII-a) can be prepared from an intermediate compound of Formula (IX-a) by removal of the protecting group being carried out according to processes known in the art.

In Reaction Scheme 6a, X is halo, PG is a protecting group, $R^c$ is $C_{1-4}$alkyl and all other variables are defined as in Formula (I).

Reaction Scheme 6a

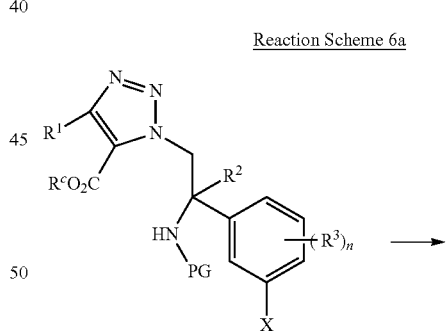

(IX-a)

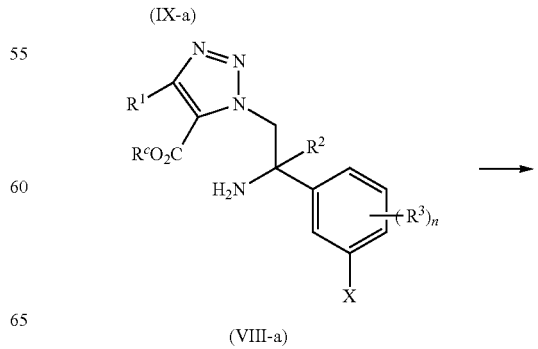

(VIII-a)

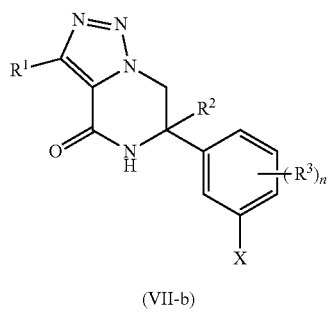

(VII-b)

Experimental Procedure 6b

Intermediate compounds of Formula (VII-c) can be prepared from the corresponding intermediates of Formula (VII-d) following art-known decarboxylation procedures. Said decarboxylation may conveniently be conducted by treatment of intermediate compounds of Formula (VII-d) with a suitable acid such as, for example, acetic acid, under suitable reaction conditions, such as at a convenient temperature, typically ranging between 100° C. and 120° C., for a period of time to ensure the completion of the reaction.

Intermediate compounds of Formula (VII-d) can be prepared from the corresponding intermediates of Formula (VII-e) following art-known ester-to-acid hydrolysis procedures. Said hydrolysis may conveniently be conducted by treatment of intermediate compounds of Formula (VII-e) with a suitable base such as, for example, lithium hydroxide, in a suitable solvent such as, for example, tetrahydrofuran and the like, or mixtures of solvents such as, for example tetrahydrofuran and water. The reaction may be carried out at a moderate temperature such as, for example rt for 2 hours.

Intermediate compounds of Formula (VII-e) can be prepared from an intermediate compound of Formula (VIII-b) following art-known cyclization procedures. Said cyclization may conveniently be conducted by heating of an intermediate compound of Formula (VIII-b) in the presence of a suitable salt such as, for example, potassium acetate, in a suitable reaction solvent, such as methanol, under suitable reaction conditions, such as at a convenient temperature, typically ranging between 80° C. and 90° C., for a period of time to ensure the completion of the reaction.

Intermediate compounds of Formula (VIII-b) can be prepared from an intermediate compound of Formula (IX-b) by removal of the protecting group being carried out according to processes known in the art.

In Reaction Scheme 6b, Z is hydrogen or halo, PG is a protecting group, $R^c$ is $C_{1-4}$alkyl, $R^d$ is $C_{1-4}$alkyl and all other variables are defined as in Formula (I).

Reaction Scheme 6b

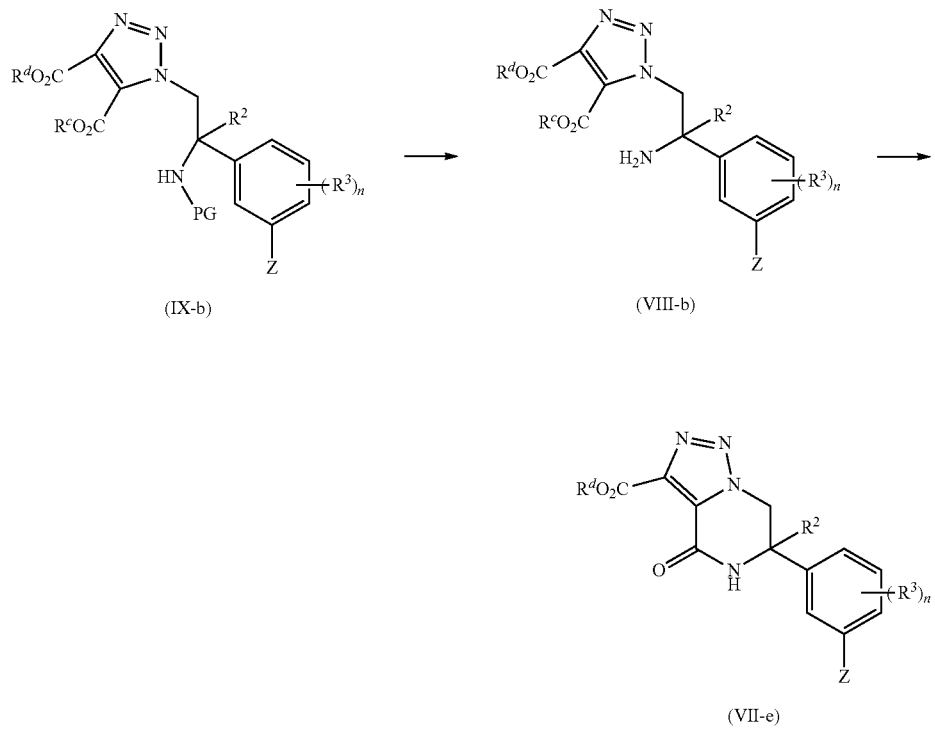

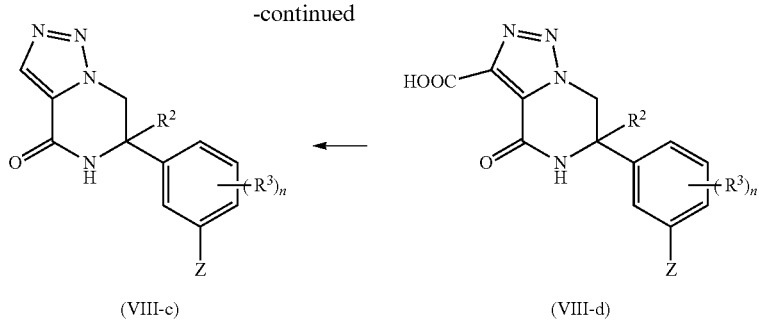

(VIII-c)  (VIII-d)

Experimental Procedure 6c

Intermediate compounds of Formula (VII-c) can be alternatively prepared from an intermediate compound of Formula (X-b) following art-known cyclization procedures. Said cyclization may conveniently be conducted by heating of an intermediate compound of Formula (X-b) in a suitable reaction solvent, such as toluene at a convenient temperature, such as, for example, 70° C., for a period of time to ensure the completion of the reaction.

Intermediate compounds of Formula (X-b) can be prepared from an intermediate compound of Formula (X-a) following art-known condensation procedures. Said condensation may be conveniently be conducted by reacting an intermediate compound of Formula (X-a) with an intermediate of Formula (XI-a) in a suitable solvent, such as dichloromethane (DCM), in the presence of a condensation agent, such as N,N'-dicyclohexylcarbodiimide (DCC) under suitable reaction conditions, such as at a convenient temperature, typically 0° C., for a period of time to ensure the completion of the reaction.

An intermediate compound of Formula (XI-a) can be obtained commercially or synthesized according to literature procedures. In Reaction Scheme 6c, Z is hydrogen or halo and all other variables are defined as in Formula (I).

Reaction Scheme 6c

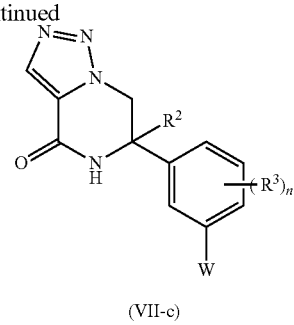

(VII-c)

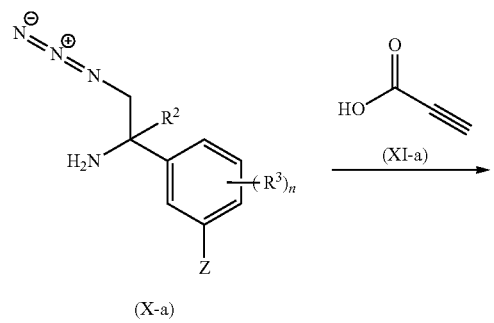

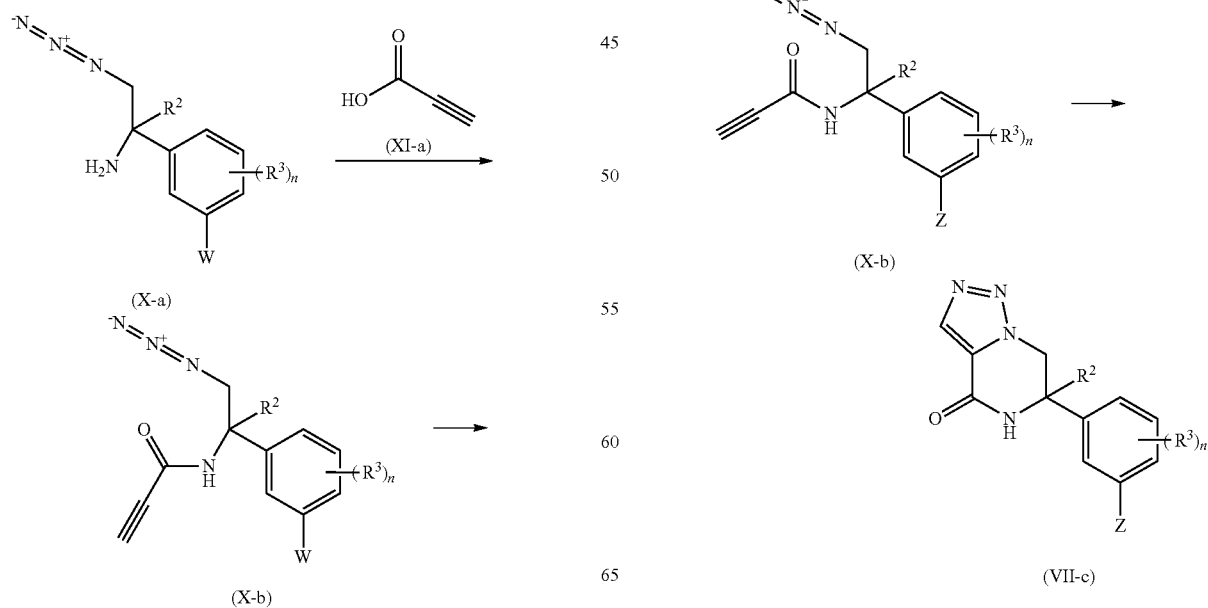

Experimental Procedure 7a

Intermediate compounds of Formula (IX-a) can be prepared from an intermediate compound of Formula (X-c) following art-known cycloaddition procedures. Said cycloaddition may conveniently be conducted by reacting an intermediate compound of Formula (X-c) with an intermediate of Formula (XI-b), in the presence of a ruthenium catalyst, such as chloro(pentamethylcyclopentadienyl)bis (triphenylphosphine)ruthenium(II), in a suitable reaction solvent, such as 1,4-dioxane, under suitable reaction conditions, such as at a convenient temperature, typically ranging between 40° C. and 80° C., for a period of time to ensure the completion of the reaction.

An intermediate compound of Formula (XI-b) can be obtained commercially or synthesized according to literature procedures. In Reaction Scheme 7a, X is halo, PG is a protecting group, $R^c$ is $C_{1-4}$alkyl and all other variables are defined as in Formula (I).

Reaction Scheme 7a

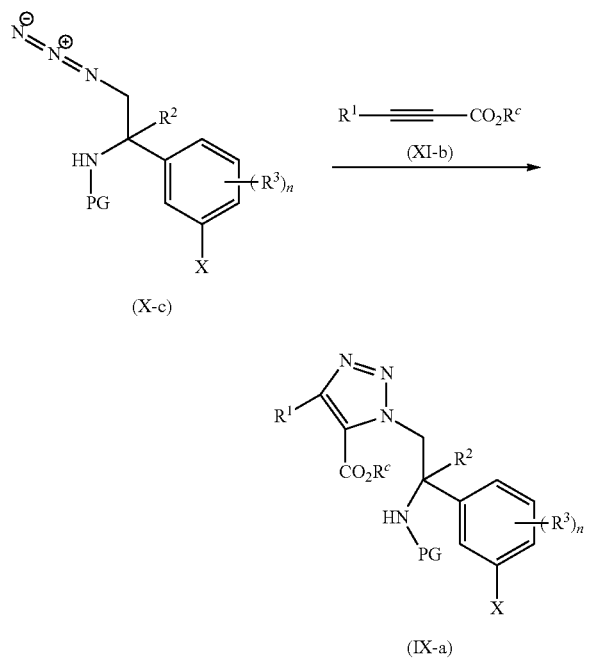

(X-c)

(IX-a)

Experimental Procedure 7b

Intermediate compounds of Formula (IX-b) can be prepared from an intermediate compound of Formula (X-d) following art-known cycloaddition procedures. Said cycloaddition may conveniently be conducted by reacting an intermediate compound of Formula (X-d) with an intermediate of Formula (XI-c) in a suitable reaction solvent, such as toluene, under suitable reaction conditions, such as at a convenient temperature, typically ranging between 90° C. and 110° C., for a period of time to ensure the completion of the reaction.

An intermediate compound of Formula (XI-c) can be obtained commercially or synthesized according to literature procedures. In Reaction Scheme 7b, Z is hydrogen or halo, PG is a protecting group, $R^c$ is $C_{1-4}$alkyl, $R^d$ is $C_{1-4}$alkyl and all other variables are defined as in Formula (I).

Reaction Scheme 7b

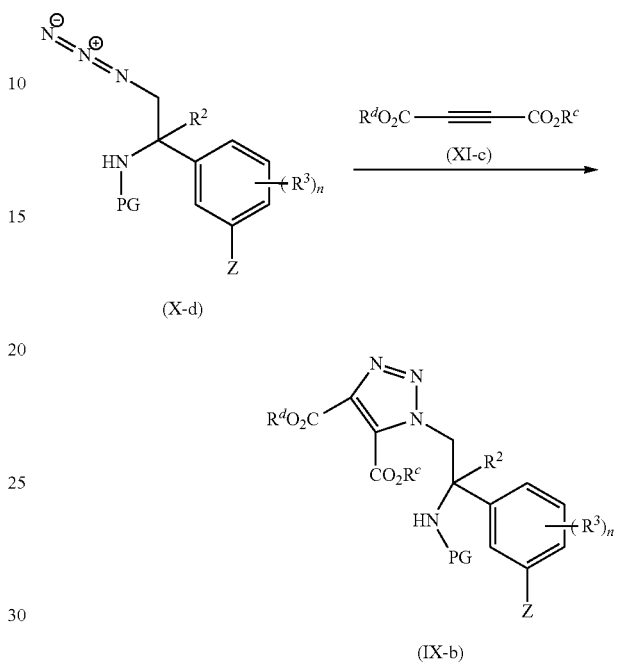

(X-d)

(IX-b)

Experimental Procedure 8

Intermediate compounds of Formula (X-a) can be prepared from an intermediate compound of Formula (X-d) by removal of the protecting group being carried out according to processes known in the art.

Intermediate compounds of Formula (X-d) can be prepared from an intermediate compound of Formula (XII), wherein PG is a protecting group of amines such as, for example, the tert-butoxycarbonyl group, following art-known alkylation procedures. Said alkylation may conveniently be conducted by treatment of (XII) with sodium azide, in a suitable inert solvent such as, DMF, under suitable reaction conditions, such as at a convenient temperature, typically ranging between 60° C. and 100° C., for a period of time to ensure the completion of the reaction.

In Reaction Scheme 8, Z is hydrogen or halo, PG is a protecting group and all other variables are defined as in Formula (I).

Reaction Scheme 8

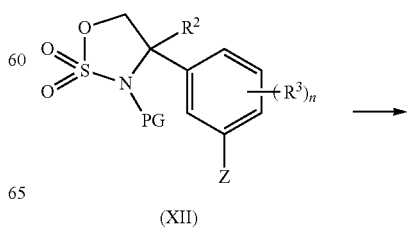

(XII)

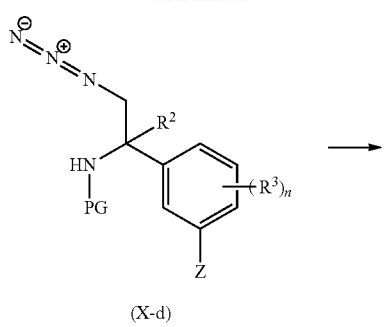

(X-d)

(X-a)

Experimental Procedure 9

Intermediate compounds of Formula (XII) can be prepared by reacting an intermediate compound of Formula (XIV) following art-known oxidation procedures. Said oxidation may conveniently be conducted by treatment of the intermediate compound of Formula (XIV) with an oxidising agent such as, for example, sodium metaperiodate in a suitable inert solvent such as, for example, acetonitrile/water, in the presence of ruthenium (III) chloride, under suitable reaction conditions, such as at a convenient temperature, typically rt, for a period of time to ensure the completion of the reaction.

Intermediate compounds of Formula (XIV) can be prepared by reacting the intermediate compounds of Formula (XIII) following art-known sulfamidate formation procedures. Said transformation may conveniently be conducted by treatment of the intermediate compound of Formula (XIII) with thionyl chloride, in the presence of a base such as, for example, pyridine, in a suitable reaction-inert solvent, such as, for example, acetonitrile, at low temperature such as, for example, −40° C., for example for 30 min and then at a moderately high temperature such as, for example, at 25° C., for example for 24 to 72 h.

Intermediate compounds of Formula (XIII) wherein X is halo and PG is a protecting group of amines such as, for example, the tert-butoxycarbonyl group, can generally be prepared following art-known Strecker type procedures described in the literature.

In Reaction Scheme 9, Z is hydrogen or halo, PG is a protecting group and all other variables are defined as in Formula (I).

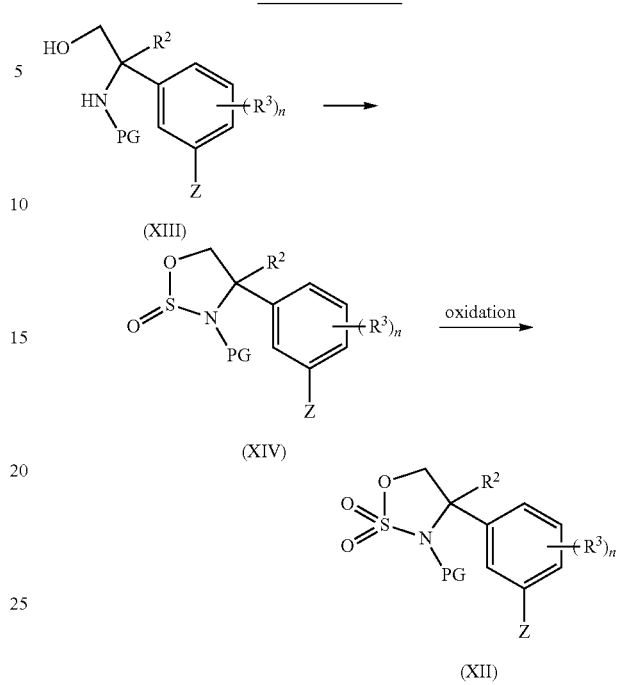

Reaction Scheme 9

(XIII)

(XIV)

(XII)

Pharmacology

The compounds of the present invention and the pharmaceutically acceptable compositions thereof inhibit BACE (BACE1 and/or BACE2) and therefore may be useful in the treatment or prevention of Alzheimer's Disease (AD), mild cognitive impairment (MCI), memory impairment, senility, dementia, dementia with Lewy bodies, dementia with progressive nuclear palsy, dementia with Cortico-basal degeneration, mixed dementia with Alzheimer's and vascular type, Alzheimer's disorder with diffuse Lewy Body disease, amyloid angiopathy, cerebral amyloid angiopathy, multi-infarct dementia, Down's syndrome, dementia associated with Parkinson's disease, dementia of the Alzheimer's type, senile dementia of the Alzheimer's type, vascular dementia, dementia due to HIV disease, dementia due to head trauma, dementia due to Huntington's disease, dementia due to Pick's disease, dementia due to Creutzfeldt-Jakob disease, frontotemporal dementia, dementia pugilistica, dementia associated with beta-amyloid, amyloidosis of the brain and other organs (age and non-age related), Dutch type of hereditary cerebral haemorrhage with amyloidosis, traumatic brain injury (TBI), temporal lobe epilepsy (TLE), hypoxia, ischemia, disruptions in cerebral metabolism, age-related macular degeneration, type 2 diabetes and other metabolic disorders, amyotrophic lateral sclerosis (ALS), multiple sclerosis (MS), arterial thrombosis, autoimmune/inflammatory diseases, cancer such as breast cancer, cardiovascular diseases such as myocardial infarction and stroke, hypertension, dermatomyositis, prion disease (Creutzfeld-Jakob disease), gastrointestinal diseases, Glioblastoma multiforme, Graves' Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple myeloma, rheumatoid arthritis, Sjogren syndrome, SpinoCerebellar Ataxia 1, SpinoCerebellar Ataxia 7, Whippel's Disease and Wilson's Disease.

As used herein, the term "treatment" is intended to refer to all processes, wherein there may be a slowing, interrupting, arresting or stopping of the progression of a disease or an alleviation of symptoms, but does not necessarily indicate a total elimination of all symptoms.

The invention relates to a compound according to the general Formula (I), a stereoisomeric form thereof or a pharmaceutically acceptable acid or base addition salt thereof, for use as a medicament.

The invention also relates to a compound according to the general Formula (I), a stereoisomeric form thereof or a the pharmaceutically acceptable acid or base addition salt thereof, for use in the treatment or prevention of diseases or conditions selected from the group consisting of Alzheimer's Disease (AD), mild cognitive impairment (MCI), memory impairment, senility, dementia, dementia with Lewy bodies, dementia with progressive nuclear palsy, dementia with Cortico-basal degeneration, mixed dementia with Alzheimer's and vascular type, Alzheimer's disorder with difuse Lewy Body disease, amyloid angiopathy, cerebral amyloid angiopathy, multi-infarct dementia, Down's syndrome, dementia associated with Parkinson's disease, dementia of the Alzheimer's type, senile dementia of the Alzheimer's type, vascular dementia, dementia due to HIV disease, dementia due to head trauma, dementia due to Huntington's disease, dementia due to Pick's disease, dementia due to Creutzfeldt-Jakob disease, frontotemporal dementia, dementia pugilistica, dementia associated with beta-amyloid, amyloidosis of the brain and other organs (age and non-age related), Dutch type of hereditary cerebral haemorrhage with amyloidosis, traumatic brain injury (TBI), temporal lobe epilepsy (TLE), hypoxia, ischemia, disruptions in cerebral metabolism, age-related macular degeneration, type 2 diabetes and other metabolic disorders, amyotrophic lateral sclerosis (ALS), multiple sclerosis (MS), arterial thrombosis, autoimmune/inflammatory diseases, cancer such as breast cancer, cardiovascular diseases such as myocardial infarction and stroke, hypertension, dermatomyositis, prion disease (Creutzfeld-Jakob disease), gastrointestinal diseases, Glioblastoma multiforme, Graves' Disease, Huntington's Disease, inclusion body myositis (IBM), inflammatory reactions, Kaposi Sarcoma, Kostmann Disease, lupus erythematosus, macrophagic myofasctitis, juvenile idiopathic arthritis, granulomatous arthritis, malignant melanoma, multiple myeloma, rheumatoid arthritis, Sjogren syndrome, SpinoCerebellar Ataxia 1, SpinoCerebellar Ataxia 7, Whippel's Disease and Wilson's Disease; in particular AD, MCI, senility, dementia, dementia with Lewy bodies, cerebral amyloid angiopathy, multi-infarct dementia, Down's syndrome, dementia associated with Parkinson's disease, dementia of the Alzheimer's type and dementia associated with beta-amyloid.

A skilled person will be familiar with alternative nomenclatures, nosologies, and classification systems for the diseases or conditions referred to herein. For example, the fifth edition of the Diagnostic & Statistical Manual of Mental Disorders (DSM-5™) of the American Psychiatric Association utilizes terms such as neurocognitive disorders (NCDs) (both major and mild), in particular, neurocognitive disorders due to Alzheimer's disease, due to traumatic brain injury (TBI), due to Lewy body disease, due to Parkinson's disease or to vascular NCD (such as vascular NCD present with multiple infarctions). Such terms may be used as an alternative nomenclature for some of the diseases or conditions referred to herein by the skilled person.

The invention also relates to the use of a compound according to the general Formula (I), a stereoisomeric form thereof or a pharmaceutically acceptable acid or base addition salt thereof, for the manufacture of a medicament for the treatment or prevention of any one of the disease conditions mentioned hereinbefore.

The invention also relates to a compound according to the general Formula (I), a stereoisomeric form thereof or a the pharmaceutically acceptable acid or base addition salt thereof, for use in the treatment, prevention, amelioration, control or reduction of the risk of diseases or conditions selected from the group consisting of Alzheimer's Disease (AD), mild cognitive impairment (MCI), memory impairment, senility, dementia, dementia with Lewy bodies, dementia with progressive nuclear palsy, dementia with Cortico-basal degeneration, mixed dementia with Alzheimer's and vascular type, Alzheimer's disorder with diffuse Lewy Body disease, amyloid angiopathy, cerebral amyloid angiopathy, multi-infarct dementia, Down's syndrome, dementia associated with Parkinson's disease, dementia of the Alzheimer's type, senile dementia of the Alzheimer's type, vascular dementia, dementia due to HIV disease, dementia due to head trauma, dementia due to Huntington's disease, dementia due to Pick's disease, dementia due to Creutzfeldt-Jakob disease, frontotemporal dementia, dementia pugilistica, dementia associated with beta-amyloid, amyloidosis of the brain and other organs (age and non-age related), Dutch type of hereditary cerebral haemorrhage with amyloidosis, traumatic brain injury (TBI), temporal lobe epilepsy (TLE), hypoxia, ischemia, disruptions in cerebral metabolism, age-related macular degeneration, type 2 diabetes and other metabolic disorders, amyotrophic lateral sclerosis (ALS), multiple sclerosis (MS), arterial thrombosis, autoimmune/inflammatory diseases, cancer such as breast cancer, cardiovascular diseases such as myocardial infarction and stroke, hypertension, dermatomyositis, prion disease (Creutzfeld-Jakob disease), gastrointestinal diseases, Glioblastoma multiforme, Graves' Disease, Huntington's Disease, inclusion body myositis (IBM), inflammatory reactions, Kaposi Sarcoma, Kostmann Disease, lupus erythematosus, macrophagic myofasctitis, juvenile idiopathic arthritis, granulomatous arthritis, malignant melanoma, multiple myeloma, rheumatoid arthritis, Sjogren syndrome, SpinoCerebellar Ataxia 1, SpinoCerebellar Ataxia 7, Whippel's Disease and Wilson's Disease; in particular AD, MCI, senility, dementia, dementia with Lewy bodies, cerebral amyloid angiopathy, multi-infarct dementia, Down's syndrome, dementia associated with Parkinson's disease, dementia of the Alzheimer's type and dementia associated with beta-amyloid; or for use in the treatment, prevention, amelioration, control or reduction of the risk of diseases or conditions selected from neurocognitive disorders due to Alzheimer's disease, due to traumatic brain injury (TBI), due to Lewy body disease, due to Parkinson's disease or to vascular NCD (such as vascular NCD present with multiple infarctions).

As already mentioned hereinabove, the term "treatment" does not necessarily indicate a total elimination of all symptoms, but may also refer to symptomatic treatment in any of the disorders mentioned above. In view of the utility of the compound of Formula (I), there is provided a method of treating subjects such as warm-blooded animals, including humans, suffering from or a method of preventing subjects such as warm-blooded animals, including humans, suffering from any one of the diseases mentioned hereinbefore.

Said methods comprise the administration, i.e. the systemic or topical administration, preferably oral administration, of a therapeutically effective amount of a compound of Formula (I), a stereoisomeric form thereof, a pharmaceutically acceptable addition salt or solvate thereof, to a subject such as a warm-blooded animal, including a human.

Therefore, the invention also relates to a method for the prevention and/or treatment of any of the diseases mentioned hereinbefore comprising administering a therapeutically effective amount of a compound according to the invention to a subject in need thereof.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent Alzheimer's disease (or by alternative nomenclatures, dementia of the Alzheimer's type, or neurocognitive disorder due to Alzheimer's disease) or the symptoms thereof, may be administered alone or in combination with one or more additional therapeutic agents. Combination therapy includes administration of a single pharmaceutical dosage formulation which contains a compound of Formula (I) and one or more additional therapeutic agents, as well as administration of the compound of Formula (I) and each additional therapeutic agents in its own separate pharmaceutical dosage formulation. For example, a compound of Formula (I) and a therapeutic agent may be administered to the patient together in a single oral dosage composition such as a tablet or capsule, or each agent may be administered in separate oral dosage formulations.

Pharmaceutical Compositions

The present invention also provides compositions for preventing or treating diseases in which inhibition of beta-secretase is beneficial, such as Alzheimer's Disease (AD), mild cognitive impairment (MCI), memory impairment, senility, dementia, dementia with Lewy bodies, dementia with progressive nuclear palsy, dementia with Cortico-basal degeneration, mixed dementia with Alzheimer's and vascular type, Alzheimer's disorder with diffuse Lewy Body disease, amyloid angiopathy, cerebral amyloid angiopathy, multi-infarct dementia, Down's syndrome, dementia associated with Parkinson's disease, dementia of the Alzheimer's type, senile dementia of the Alzheimer's type, vascular dementia, dementia due to HIV disease, dementia due to head trauma, dementia due to Huntington's disease, dementia due to Pick's disease, dementia due to Creutzfeldt-Jakob disease, frontotemporal dementia, dementia pugilistica, dementia associated with beta-amyloid, amyloidosis of the brain and other organs (age and non-age related), Dutch type of hereditary cerebral haemorrhage with amyloidosis, traumatic brain injury (TBI), temporal lobe epilepsy (TLE), hypoxia, ischemia, disruptions in cerebral metabolism, age-related macular degeneration, type 2 diabetes and other metabolic disorders, amyotrophic lateral sclerosis (ALS), multiple sclerosis (MS), arterial thrombosis, autoimmune/inflammatory diseases, cancer such as breast cancer, cardiovascular diseases such as myocardial infarction and stroke, hypertension, dermatomyositis, prion disease (Creutzfeld-Jakob disease), gastrointestinal diseases, Glioblastoma multiforme, Graves' Disease, Huntington's Disease, inclusion body myositis (IBM), inflammatory reactions, Kaposi Sarcoma, Kostmann Disease, lupus erythematosus, macrophagic myofasctitis, juvenile idiopathic arthritis, granulomatous arthritis, malignant melanoma, multiple myeloma, rheumatoid arthritis, Sjogren syndrome, SpinoCerebellar Ataxia 1, SpinoCerebellar Ataxia 7, Whippel's Disease and Wilson's Disease; in particular Alzheimer's disease (AD), mild cognitive impairment, senility, dementia, dementia with Lewy bodies, Down's syndrome, dementia associated with stroke, dementia associated with Parkinson's disease, dementia of the Alzheimer's type and dementia associated with beta-amyloid. According to alternative nomenclatures, the present invention provides compositions for preventing or treating diseases in which inhibition of beta-secretase is beneficial, such as neurocognitive disorders due to Alzheimer's disease, due to traumatic brain injury (TBI), due to Lewy body disease, due to Parkinson's disease or to vascular NCD (such as vascular NCD present with multiple infarctions). Said compositions comprising a therapeutically effective amount of a compound according to formula (I) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy. A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound according to formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

For the compositions and methods provided above, one of skill in the art will understand that preferred compounds for use in each are those compounds that are noted as preferred above. Still further preferred compounds for the compositions and methods are those compounds provided in the examples below.

Experimental Part

The following examples are intended to illustrate but not to limit the scope of the present invention.

Chemistry

Several methods for preparing the compounds of this invention are illustrated in the following Examples. Unless otherwise noted, all starting materials were obtained from commercial suppliers and used without further purification.

Hereinafter, "Boc" means tert-butyloxycarbonyl; "CI" means chemical ionisation; "DAD" means diode-array detector; "DCM" means dichloromethane; "DIPE" means diisopropylether; "DMF" means N,N-dimethylformamide; "DMSO" means dimethylsulfoxide; "Et$_2$O" means diethylether; "EtOAc" means ethyl acetate; "EtOH" means ethanol; "ES" means electrospray; "h" means hours; "iPrOH" means isopropanol; "L" means liter; "LRMS" means low-resolution mass spectrometry/spectra; "HPLC" means high performance liquid chromatography; "HRMS" means high-resolution mass spectra/spectrometry; "MeOH" means methanol; "NH$_4$Ac" means ammonium acetate; "eq" means equivalent; "RP" means Reversed Phase; "rt" means room temperature; "M.p." means melting point; "min" means minutes; "s" means second(s); "TOF" means time of flight; "sat." means saturated; "SFC" means supercritical fluid chromatography; "sol." means solution, "TEA" means triethylamine; "THF" means tetrahydrofuran, "(±)-BINAP" means 2,2'-Bis(diphenylphosphino)-1,1'-binaphthalene, "DCC" means N,N'-dicyclohexylcarbodiimide, "DMTMM" means 4-(4,6-dimethoxy-1,3,5-triazin-2-yl)-4-methylmorpholinium chloride; "RS" next to asymmetric centres in chemical structures means racemic.

Thin layer chromatography (TLC) was carried out on silica gel 60 F254 plates (Merck) using reagent grade solvents. Open column chromatography was performed on silica gel, particle size 60 Å, mesh=230-400 (Merck) using standard techniques. Automated flash column chromatography normal phase was performed using Biotage® Isolera™ 4 or Biotage® SP-1. Automated flash column chromatography reversed phase was performed using (a) a GILSON® Semi-Preparative System, operated by Trilution® software, equipped with a Phenomenex Gemini® C18 100A column (100 mm long×30 mm I.D.; 5 μm particles) at 25° C., with a flow rate of 40 mL/min or (b) a GILSON® Semi-Preparative System, operated by Unipoint software, equipped with a Phenomenex Gemini® C18 100A column (100 mm long×21.2 mm I.D.; 5 μm particles) at 25° C., with a flow rate of 20 mL/min.

For key intermediates, as well as some final compounds, the absolute configuration of chiral centers (indicated as R and/or S) were established via comparison with samples of known configuration, or the use of analytical techniques suitable for the determination of absolute configuration, such as VCD (vibrational circular dichroism) or X-ray crystallography.

Synthesis of Intermediate Compounds

Intermediate 1 (I-1)

(R)-[2-Azido-1-(5-bromo-2-fluoro-phenyl)-1-methyl-ethyl]-carbamic acid tert-butyl ester (I-1)

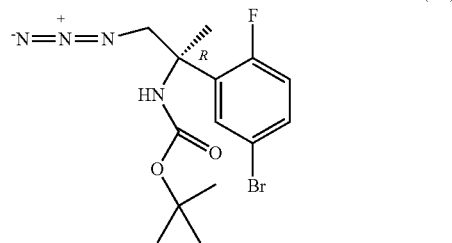

Sodium azide (2.38 g, 36.6 mmol) was added to a sol. of (4R)-4-(5-bromo-2-fluorophenyl)-4-methyl-1,2,3-oxathiazolidine-3-carboxylic acid 1,1-dimethylethyl ester [CAS 1398113-03-5] (5 g, 12.2 mmol) in DMF (40 mL). The mixture was stirred at 80° C. for 2 h. Then, a sat. sol. of citric acid was added and the mixture was stirred for 4 h. The solvent was evaporated in vacuo. Water was added and extracted with DCM. The organic layer was separated, dried (MgSO$_4$), filtered and the solvents evaporated in vacuo to yield intermediate I-1 (4.5 g, 99%) that was used in the next step without further purification.

Intermediate 2 (I-2)

(R)-3-[2-(5-Bromo-2-fluoro-phenyl)-2-tert-butoxycarbonylamino-propyl]-3H-[1,2,3]triazole-4-carboxylic acid methyl ester (I-2)

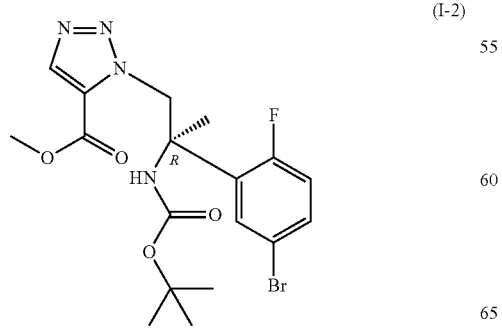

Intermediate compound I-1 (0.91 g, 2.4 mmol) and methyl propiolate (0.22 mL, 2.4 mmol) was added to chloro(pentamethylcyclopentadienyl)bis-(triphenylphosphine)ruthenium(II) (39 mg, 0.04 mmol) in 1,4-dioxane (9 mL). The vial was purged with nitrogen and the mixture was stirred at 60° C. for 6 h. Methyl propiolate (0.22 mL, 2.4 mmol) and chloro(pentamethylcyclopentadienyl)bis-(triphenylphosphine)ruthenium(II) (39 mg, 0.04 mmol) were added. The mixture was stirred at 60° C. for 16 h. Then additional methyl propiolate (0.22 mL, 2.4 mmol) and chloro(pentamethylcyclopentadienyl)bis(triphenylphosphine)ruthenium(II) (39 mg, 0.04 mmol) were added. The mixture was stirred at 60° C. for 16 h. The solvent was evaporated in vacuo. The crude product was purified by flash column chromatography (silica; EtOAc in heptane 0/100 to 30/70). The desired fractions were collected and the solvents evaporated in vacuo to yield intermediate I-2 (228 mg, 20%).

Intermediate 3 (I-3)

(R)-3-[2-Amino-2-(5-bromo-2-fluoro-phenyl)-propyl]-3H-[1,2,3]triazole-4-carboxylic acid methyl ester (I-3)

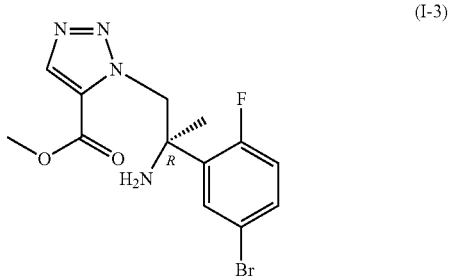

Trifluoroacetic acid (1.3 mL, 16.8 mmol) was added to a sol. of intermediate compound I-2 (154 mg, 0.34 mmol) in DCM (3.1 mL). The mixture was stirred at rt for 1 h. The solvent was evaporated in vacuo. DCM was added and the organic phase was washed with a sat. sol. NaHCO$_3$. The organic layer was separated, dried (MgSO$_4$), filtered and the solvents evaporated in vacuo to yield intermediate I-3 (120 mg, 93% purity, quant.) that was used in the next step without further purification.

Intermediate 4 (I-4)

(R)-6-(5-Bromo-2-fluoro-phenyl)-6-methyl-6,7-dihydro-5H-[1,2,3]triazolo[1,5-a]pyrazin-4-one (I-4)

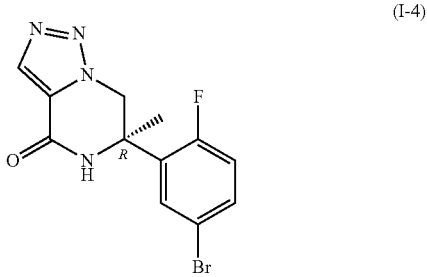

Intermediate compound I-3 (1.7 g, 4.76 mmol) in DMF (42 mL) was stirred at 100° C. for 48 h. The solvent was evaporated in vacuo. The crude product was purified by flash column chromatography (silica; EtOAc in DCM 0/100 to 20/80). The desired fractions were collected and the solvents evaporated in vacuo to yield intermediate I-4 (1.12 g, 72%) as a white powder.

Intermediate 5 (I-5)

(R)-6-(5-Bromo-2-fluoro-phenyl)-6-methyl-6,7-di-hydro-5H-[1,2,3]triazolo[1,5-a]pyrazine-4-thione (I-5)

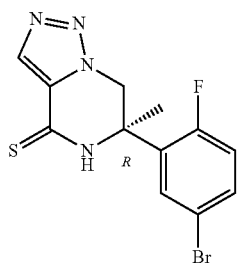

THF (20.4 mL) was added to a mixture of phosphorus pentasulfide (2.19 g, 9.9 mmol) and intermediate compound I-4 (1.07 g, 3.3 mmol). The mixture was stirred at 70° C. for 30 min. Then EtOAc was added and the mixture was filtered through diatomaceous earth. The solvent was evaporated in vacuo and the crude product was purified by flash column chromatography (silica; EtOAc in heptane 0/100 to 100/0). The desired fractions were collected and the solvents evaporated in vacuo to yield intermediate I-5 (882 mg, 78%).

Intermediate 6 (I-6)

(R)-6-(5-Bromo-2-fluoro-phenyl)-6-methyl-6,7-di-hydro-5H-[1,2,3]triazolo[1,5-a]pyrazin-4-one (I-6)

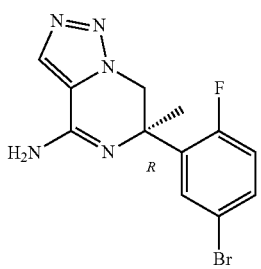

In a sealed tube, a sol. of intermediate compound I-5 (880 mg, 2.6 mmol) in 7 M sol. of ammonia in MeOH (44 mL) was stirred at 70° C. for 16 h. Then the solvent was evaporated in vacuo and fresh 7 M sol. of ammonia in MeOH (44 mL) was added. The mixture was stirred at 70° C. for 24 h. Then the solvent was evaporated in vacuo. The crude product was purified by flash column chromatography (silica; 7M ammonia in MeOH in DCM 0/100 to 15/85). The desired fractions were collected and the solvents evaporated in vacuo. The solid was dissolved in EtOAc and washed with a sat. sol. of NaHCO₃. The organic layer was separated, dried (MgSO₄), filtered and the solvents evaporated in vacuo to yield intermediate I-6 (759 mg, 91%) as a white solid.

Intermediate 7 (I-7)

(R)-6-(5-Amino-2-fluoro-phenyl)-6-methyl-6,7-di-hydro-5H-[1,2,3]triazolo[1,5-a]pyrazin-4-one (I-7)

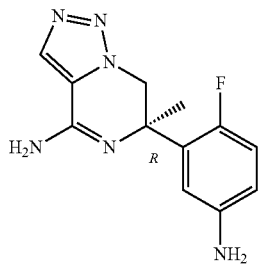

Sodium azide (326 mg, 5.0 mmol), copper(I) iodide (477 mg, 2.5 mmol) and Na₂CO₃ (425 mg, 4.0 mmol) were added to a sol. of intermediate compound I-6 (650 mg, 2.0 mmol) in DMSO (29 mL). After the mixture was well degassed, N,N'-dimethylethylenediamine (0.38 mL, 3.5 mmol) was added. The mixture was stirred at 110° C. for 5 h. The mixture was diluted with DCM and washed with a NH₃ sol. The aqueous phase was extracted several times with DCM/10% MeOH and EtOAc/THF 1:1. The organic layer was separated, dried (MgSO₄), filtered and the solvents evaporated in vacuo. The crude product was purified by flash column chromatography (silica; 7M ammonia in MeOH in DCM 0/100 to 5/95). The desired fractions were collected and the solvents evaporated in vacuo to yield intermediate I-7 (357 mg, 68%).

Intermediate 8 (I-8)

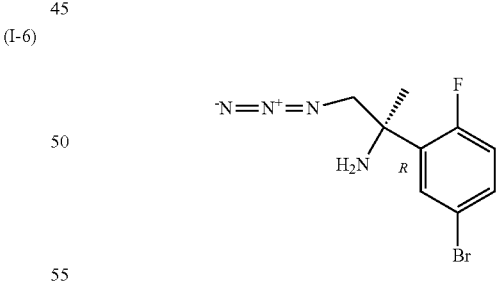

4M HCl solution in 1,4-dioxane (21 mL, 85.74 mmol) was added to a solution of intermediate I-1 (3.2 g, 8.57 mmol) in 1,4-dioxane (11 mL). The reaction mixture was stirred at rt for 24 h. Excess of HCl was removed by bubbling nitrogen through the reaction mixture. Then the reaction mixture was cooled down to 0° C. and sat. aq. NaHCO₃ solution was added until pH basic. The aqueous layer was extracted with EtOAc. The organic layer was separated, dried (MgSO₄), filtered and the solvents evaporated in vacuo to afford intermediate I-8 (2.12 g, 91%), as a colourless oil.

Intermediate 9 (I-9)

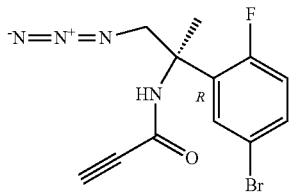

Propiolic acid (0.71 mL, 11.5 mmol) was added to a solution of DCC (2.54 g, 12.30 mmol) in DCM (30 mL) at 0° C. A solution of intermediate I-8 (2.1 g, 7.69 mmol) in DCM (20 mL) was added dropwise and the reaction mixture was stirred at 0° C. for 2 h.

The precipitate was filtered off and washed with DCM. The filtrate was concentrated in vacuo, keeping the temperature below 25° C. until a small volume (5-10 mL) of solution was left. The resulting crude product was purified by flash column chromatography (silica; DCM). The desired fractions were collected and the solvents evaporated in vacuo keeping the temperature below 25° C. to yield intermediate I-9 (2.2 g, 89%).

Intermediate 10 (I-10)

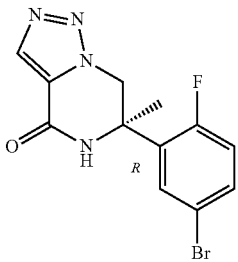

Intermediate compound I-9 (2.2 g, 6.77 mmol) was stirred in toluene (220 mL) at 70° C. for 18 h. The solvent was evaporated in vacuo. The crude product was purified by flash column chromatography (silica; EtOAc in DCM 0/100 to 40/60). The desired fractions were collected and the solvents evaporated in vacuo to yield intermediate I-10 (2.15 g, 98%) as a white solid.

Intermediate 11 (I-11)

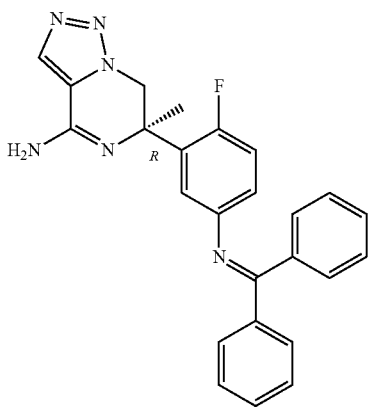

Toluene (36 mL) was added to a mixture of intermediate I-10 (1.8 g, 5.16 mmol), tris(dibenzylideneacetone)dipalladium(0) (0.472 g, 0.52 mmol), (±)-BINAP (0.965 g, 1.55 mmol) and sodium tert-butoxide (0.893 g, 9.30 mmol) under $N_2$ at rt. After the mixture was well degassed, benzophenone imine (1.7 mL, 10.33 mmol) was added. The mixture was stirred at 90° C. for 18 h. The reaction mixture was concentrated in vacuo and the crude was diluted with water and extracted with DCM. The organic layer was separated, dried ($MgSO_4$), filtered and the solvents evaporated in vacuo. The crude product was purified by flash column chromatography (silica; MeOH in DCM 0/100 to 10/90). The desired fractions were collected and the solvents evaporated in vacuo to yield intermediate I-11 (1.63 g, 73%) as a pale yellow solid.

Intermediate 12 (I-12)

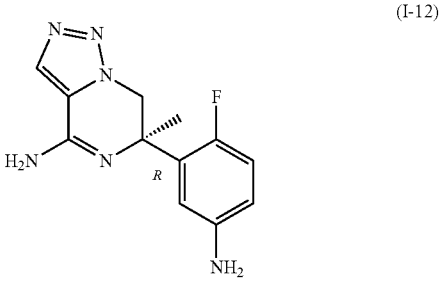

Aq. HCl (37% in $H_2O$, 4.1 mL, 49.47 mmol) was added to a solution of intermediate I-11 (2.1 g, 4.95 mmol) in isopropanol (21 mL). The mixture was stirred at rt for 2 h. The mixture was concentrated in vacuo and the residue triturated in $Et_2O$. The solid was filtered off and dissolved in isopropanol. $NaHCO_3$ (0.415 g, 4.95 mmol) was added and the mixture was stirred for 1 h until pH basic. The mixture was filtered and the filtrate was concentrated in vacuo. The crude product was purified by flash column chromatography (silica; 7M $NH_3$ in MeOH in DCM 0/100 to 20/80). The desired fractions were collected and the solvents evaporated in vacuo to yield intermediate I-12 (1.2 g, 93%) as a pale yellow solid.

Intermediate 13 (I-13)

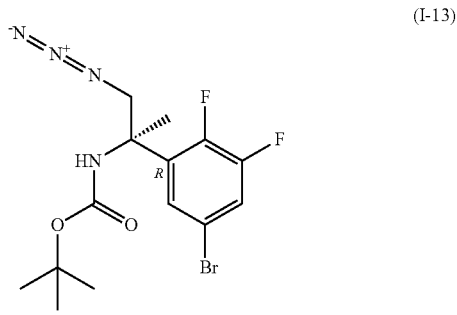

Intermediate I-13 was prepared following a synthetic procedure similar to the one reported for the synthesis of intermediate I-1. Starting from tert-butyl (4R)-4-(5-bromo-2,3-difluoro-phenyl)-4-methyl-2,2-dioxo-oxathiazolidine-3-carboxylate (6.5 g, 15.18 mmol, prepared similarly to the procedure described for the synthesis of [CAS 1398113-03-5] in WO2012/120023) intermediate I-13 was obtained (6 g, 100%) as a colourless oil.

Intermediate 14 (I-14)

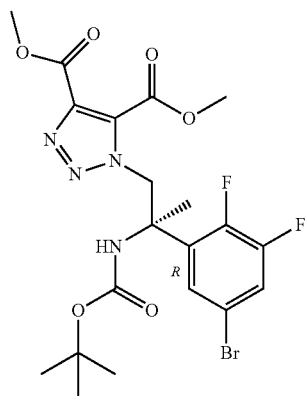
(I-14)

Dimethyl acetylenedicarboxylate (1.6 mL, 13.29 mmol) was added to a solution of intermediate I-13 (5.2 g, 13.29 mmol) in toluene (50 mL) and the reaction mixture was stirred at 110° C. for 18 h. The solvent was evaporated in vacuo to yield intermediate I-14 (12.5 g, quant. yield), which was used as such in the next reaction step.

Intermediate 15 (I-15)

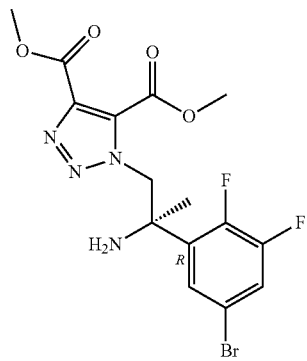
(I-15)

Intermediate I-14 (12.5 g, 15 mmol) was added to HCl (4 M in dioxane, 37.5 mL, 150 mmol) and the reaction mixture was stirred at rt for 2 hours. The solvent was evaporated in vacuo to yield intermediate I-15 (8.5 g, quant. yield), which was used as such in the next reaction step.

Intermediate 16 (I-16)

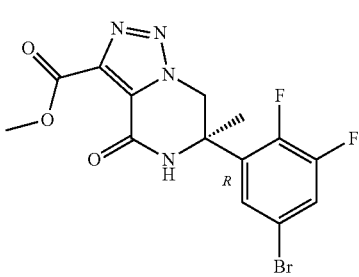
(I-16)

Potassium acetate (4.423 g, 45.06 mmol) was added to a solution of intermediate I-15 (8.5 g, 15.02 mmol) in MeOH (62 mL). The reaction mixture was stirred at 90° C. in a sealed tube for 1 h. The reaction was cooled down and the solvent evaporated in vacuo.

The crude was suspended in DCM and washed with water. The organic layer was separated, dried (MgSO$_4$), filtered and the solvents evaporated in vacuo to afford intermediate I-16 (4.8 g, 76%), which was used as such in the next reaction step.

Intermediate 17 (I-17)

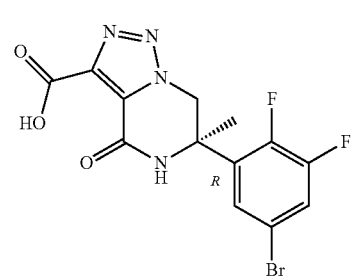
(I-17)

A solution of lithium hydroxide (0.816 g, 34.10 mmol) in water (19 mL) was added to a solution of intermediate I-16 (4.8 g, 11.37 mmol) in THF (76 mL). The reaction mixture was stirred at rt for 3 h. Then the organic layer was removed. Aq. 1N HCl was added to the aqueous layer until pH=2. The precipitate was collected by filtration, washed with water and dried (vacuum oven, 50° C.) to afford intermediate I-17 (3.9 g, 89%).

Intermediate 18 (I-18)

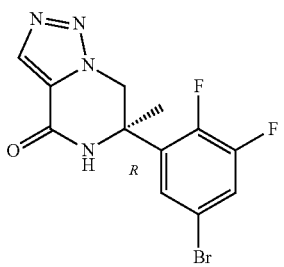
(I-18)

A solution of intermediate I-17 (3.33 g, 8.60 mmol) in acetic acid (10 mL, 172.03 mmol) was stirred at 120° C. for 18 h. The reaction was concentrated in vacuo and the crude product was purified by flash column chromatography (silica; EtOAc in DCM 0/100 to 40/60). The desired fractions were collected and the solvents evaporated in vacuo to yield intermediate I-18 (2.9 g, 98%).

Intermediate 19 (I-19)

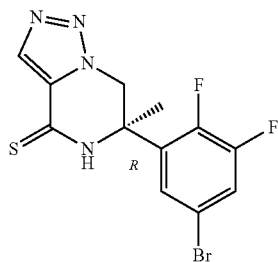

Intermediate I-19 was prepared following a synthetic procedure similar to the one reported for the synthesis of intermediate I-5. Starting from intermediate I-18 (3.7 g, 10.78 mmol) intermediate I-19 was obtained (3.5 g, 90%).

Intermediate 20 (I-20)

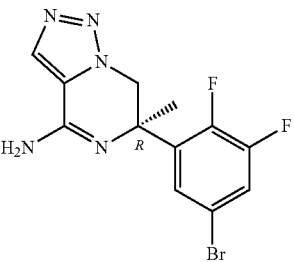

Intermediate I-20 was prepared following a synthetic procedure similar to the one reported for the synthesis of intermediate I-6. Starting from intermediate I-19 (3.5 g, 9.74 mmol) intermediate I-20 was obtained (3.4 g, 82%).

Intermediate 21 (I-21)

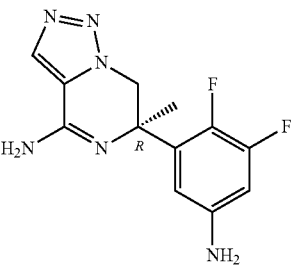

Intermediate I-21 was prepared following a synthetic procedure similar to the one reported for the synthesis of intermediate I-7. Starting from intermediate I-20 (0.35 g, 0.82 mmol) intermediate I-21 was obtained (0.15 g, 66%).

Intermediate 22 (I-22)

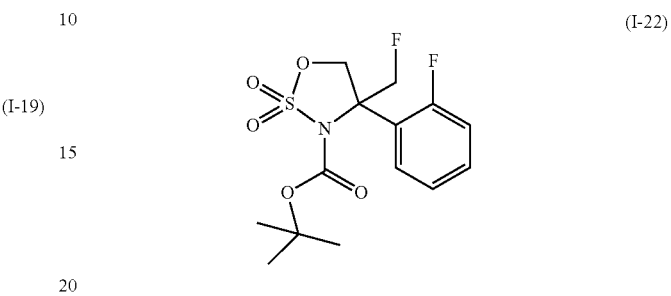

Intermediate I-22 was prepared following a synthetic sequence similar to the one reported for the synthesis of (4R)-4-(5-bromo-2-fluorophenyl)-4-methyl-1,2,3-oxathiazolidine-3-carboxylic acid 1,1-dimethylethyl ester [CAS 1398113-03-5] starting from 2-fluoro-1-(2-fluorophenyl)ethanone [CAS 1402412-84-3].

Intermediate 23 (I-23)

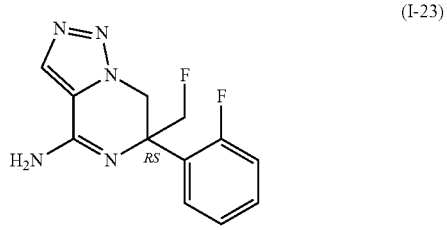

By following a synthetic sequence involving procedures similar to the ones used for the synthesis of (in the order) intermediate I-13, intermediate I-14, intermediate I-15, intermediate I-16, intermediate I-17, intermediate I-18, intermediate I-5 and intermediate I-6, intermediate I-23 was obtained starting from intermediate I-22.

Intermediate 24 (I-24)

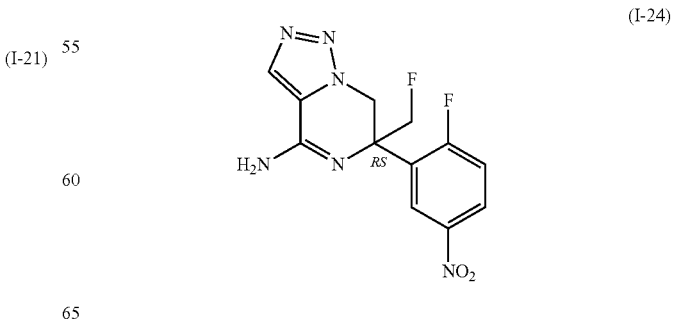

Intermediate I-23 (0.8 g, 3.04 mmol) was added to fuming nitric acid (10 mL, 233.36 mmol) at 0° C. and the reaction mixture was stirred at this temperature for 30 min. Ice water was added to the reaction mixture and aq. 50% NaOH sol was added until pH basic. The aqueous layer was extracted with DCM. The organic layer was dried (MgSO$_4$), filtered and evaporated in vacuo to yield intermediate I-24 (0.3 g, 32%) as a solid.

Intermediate 25 (I-25)

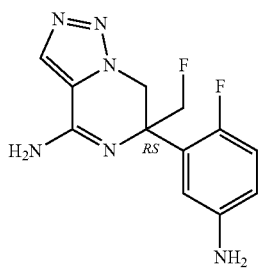

(I-25)

Intermediate I-24 (0.41 g, 1.33 mmol) was dissolved in MeOH (45 mL) and water (14 mL). Iron (0.6 g, 10.74 mmol) and ammonium chloride (0.56 g, 10.47 mmol) were added and the reaction mixture was stirred at 70° C. for 1 h. Then extra iron (0.6 g, 10.74 mmol) and ammonium chloride (2.11 g, 39.45 mmol) were added. The reaction mixture was stirred at 70° C. for another 2 h. After cooling, the reaction mixture was filtered through diatomaceous earth and washed with MeOH, H$_2$O and EtOAc. The filtrate was concentrated in vacuo and the residue was dissolved with sat. aq. NaHCO$_3$ solution and EtOAc. The organic layer was separated, dried (MgSO$_4$), filtered and concentrated in vacuo to yield intermediate I-25 (150 mg, 40%), which was used as such in the next reaction step.

Final Compounds

Example E1

N-{3-[(6R)-4-amino-6-methyl-6,7-dihydro[1,2,3]triazolo[1,5-a]pyrazin-6-yl]-4-fluorophenyl}-5-fluoropyridine-2-carboxamide (compound 1)

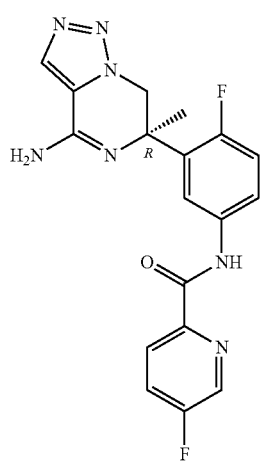

compound 1

1M aqueous HCl sol. (0.29 mL, 0.3 mmol) was added to intermediate compound I-7 (75 mg, 0.3 mmol) in MeOH (1.5 mL) at rt. Then 5-fluoro-2-pyridine carboxylic acid (41 mg, 0.3 mmol) and 1-(3-dimethylaminopropyl)-3-ethylcarbodiimide hydrochloride (66 mg, 0.4 mmol) were added. The mixture was stirred at rt for 3 h. A sat. sol. of Na$_2$CO$_3$ was added and the mixture was extracted with DCM. The organic layer was separated, washed with brine, dried (MgSO$_4$), filtered and the solvents evaporated in vacuo. The crude product was purified by flash column chromatography (silica; 7M ammonia in MeOH in DCM 0/100 to 10/90). The desired fractions were collected and the solvents evaporated in vacuo to yield compound 1 as a white solid (79 mg, 71%).

Example E2

N-{3-[(6R)-4-Amino-6-methyl-6,7-dihydro[1,2,3]triazolo[1,5-a]pyrazin-6-yl]-4-fluorophenyl}-4-chloro-1-(difluoromethyl)-1H-pyrazole-3-carboxamide (compound 5)

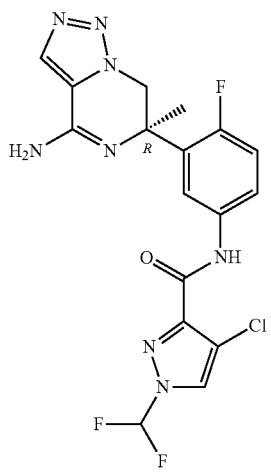

compound 5

4-Chloro-1-(difluoromethyl)-1H-pyrazole-3-carboxylic acid (0.083 g, 0.423 mmol) was added to DMTMM (0.117 g, 0.423 mmol) in MeOH (2 mL). After stirring the mixture for 5 minutes, a solution of intermediate I-12 (0.1 g, 0.384 mmol) in MeOH (2 mL) was added at 0° C., and the mixture was stirred for 24 hours. The solvent was evaporated in vacuo. The residue was then suspended in DCM and treated with sat. aq. Na$_2$CO$_3$ sol. The organic layer was separated, dried (MgSO$_4$), filtered and the solvents evaporated in vacuo. The crude product was purified by flash column chromatography (silica gel; 7 M ammonia in MeOH/DCM 0/100 to 5/95). The desired fractions were collected and concentrated in vacuo. The product was purified further by preparative HPLC (RP, C18 XBridge 30×100 5 um), mobile phase (gradient 90% 0.1% to 0% 0.1% NH$_4$HCO$_3$/NH$_4$OH pH 9 solution in water, 10% MeCN). The desired fractions were collected and the product was extracted with DCM. The organic layer was separated, dried (MgSO$_4$), filtered and concentrated in vacuo. The residue was dried overnight (vacuum oven, 50° C.) yielding compound 5 (53 mg, 31% yield) as a pale yellow solid.

Example E3

N-{3-[(6R)-4-Amino-6-methyl-6,7-dihydro[1,2,3]triazolo[1,5-a]pyrazin-6-yl]-4,5-difluorophenyl}-5-fluoropyridine-2-carboxamide (compound 8)

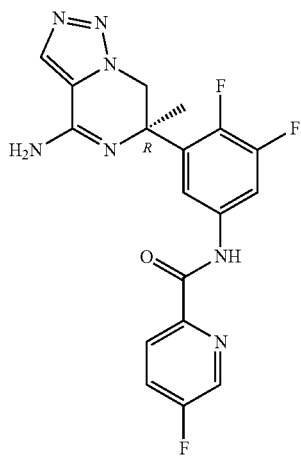

compound 8

5M HCl sol. in 2-propanol (0.11 mL, 0.54 mmol) was added to intermediate I-21 (150 mg, 0.54 mmol) in MeOH (4 mL) at rt. Then 5-fluoro-2-pyridine carboxylic acid (76 mg, 0.54 mmol) and 1-(3-dimethylaminopropyl)-3-ethylcarbodiimide hydrochloride (124 mg, 0.65 mmol) were added. The mixture was stirred at rt for 3 h. Sat. aq. $Na_2CO_3$ sol. was added and the mixture was extracted with DCM. The organic layer was separated, washed with brine, dried ($MgSO_4$), filtered and the solvents evaporated in vacuo. The crude product was purified by flash column chromatography (silica; 7M ammonia in MeOH in DCM 0/100 to 5/95). The desired fractions were collected and the solvents evaporated in vacuo to afford a solid, which was suspended in DIPE, filtered and dried (vacuum oven, 50° C.) yielding compound 8 as a white solid (160 mg, 74%).

Example E4

(rac)-N-{3-[4-amino-6-(fluoromethyl)-6,7-dihydro[1,2,3]triazolo[1,5-a]pyrazin-6-yl]-4-fluorophenyl}-5-fluoropyridine-2-carboxamide (compound 9),
N-{3-[(6R)-4-amino-6-(fluoromethyl)-6,7-dihydro[1,2,3]triazolo[1,5-a]pyrazin-6-yl]-4-fluorophenyl}-5-fluoropyridine-2-carboxamide (compound 10),
N-{3-[(6S)-4-amino-6-(fluoromethyl)-6,7-dihydro[1,2,3]triazolo[1,5-a]pyrazin-6-yl]-4-fluorophenyl}-5-fluoropyridine-2-carboxamide (compound 11)

compound 9

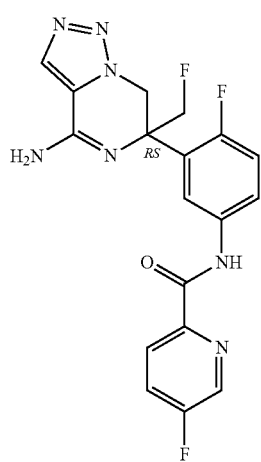

compound 10

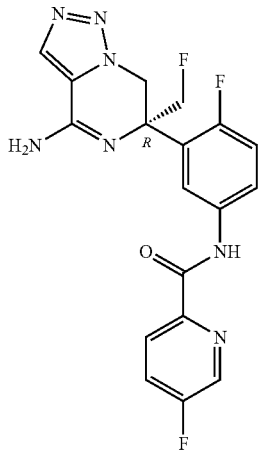

compound 11

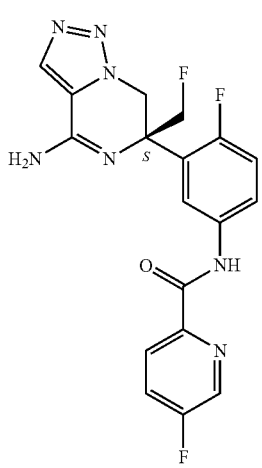

HCl (6 M in iPrOH, 0.23 mL, 1.35 mmol) was added to intermediate I-25 (250 mg, 0.90 mmol) in MeOH (7 mL) at rt. Then 5-fluoro-2-pyridine carboxylic acid (139 mg, 0.99 mmol) and 1-(3-dimethylaminopropyl)-3-ethylcarbodiimide hydrochloride (224 mg, 1.17 mmol) were added. The mixture was stirred at rt for 2 h. Sat. aq. $Na_2CO_3$ sol. was added and the mixture was extracted with DCM. The organic layer was separated, washed with brine, dried ($MgSO_4$), filtered and the solvents evaporated in vacuo. The crude product was purified by flash column chromatography (silica; 7M ammonia in MeOH in DCM 0/100 to 3/97). The desired fractions were collected and the solvents evaporated in vacuo to yield compound 9 as a racemate (115 mg, 32%). This product was then purified by preparative SFC on Chiralpak Diacel AD (20×250 mm), mobile phase ($CO_2$, MeOH with 0.4% $iPrNH_2$), yielding compound 10 (40 mg, 11%) and compound 11 (40 mg, 11%).

Table 1 below lists additional compounds of Formula (I).

TABLE 1

The following compounds were prepared following the methods exemplified in the Experimental Part (Ex. No.). Compounds exemplified and described in the experimental part are marked with an asterisk *.

| Co. No. | Ex. No. | R¹ | R² | R³ | R⁴ |
|---|---|---|---|---|---|
| 1 | E1* | H | Me (R) | a-F | —NH-C(O)-(5-F-pyridin-2-yl) |
| 2 | E1 | H | Me (R) | a-F | —NH-C(O)-(5-CN-pyridin-2-yl) |
| 3 | E1 | H | Me (R) | a-F | —NH-C(O)-(5-OMe-pyrazin-2-yl) |
| 4 | E1 | H | Me (R) | a-F | —NH-C(O)-(5-Cl-pyridin-2-yl) |
| 5 | E2 | H | Me (R) | a-F | —NH-C(O)-(1-CHF₂-4-Cl-pyrazol-3-yl) |
| 6 | E2 | H | Me (R) | a-F | —NH-C(O)-(5-OCH₂CF₃-pyrazin-2-yl) |
| 7 | E1 | H | Me (R) | a-F | —NH-C(O)-(5-OCH₂F-pyridin-2-yl) |
| 8 | E3 | H | Me (R) | a-F, b-F | —NH-C(O)-(5-F-pyridin-2-yl) |
| 9 | E4 | H | CH₂F (RS) | a-F | —NH-C(O)-(5-F-pyridin-2-yl) |

TABLE 1-continued

The following compounds were prepared following the methods exemplified in the Experimental Part (Ex. No.). Compounds exemplified and described in the experimental part are marked with an asterisk *.

| Co. No. | Ex. No. | R¹ | R² | R³ | R⁴ |
|---|---|---|---|---|---|
| 10 | E4 | H | CH₂F (R) | a-F | —NH-C(O)-(5-F-pyridin-2-yl) |
| 11 | E4 | H | CH₂F (S) | a-F | —NH-C(O)-(5-F-pyridin-2-yl) |

Analytical Part

LCMS

LCMS General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times ($R_t$) and ions. If not specified differently in the table of data, the reported molecular ion corresponds to the [M+H]⁺ (protonated molecule) and/or [M−H]⁻ (deprotonated molecule). In case the compound was not directly ionizable the type of adduct is specified (i.e. [M+NH₄]⁺, [M+HCOO]⁻, etc. . . . ). For molecules with multiple isotopic patterns (Br, Cl . . . ), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica., "Q-Tof" Quadrupole Time-of-flight mass spectrometers, "CLND", ChemiLuminescent Nitrogen Detector, "ELSD" Evaporative Light Scanning Detector.

TABLE 2A

LCMS Method codes (Flow expressed in mL/min; column temperature (T) in ° C.; Run time in minutes).

| Method code | Instrument | Column | Mobile phase | Gradient | Flow Col T | Run time |
|---|---|---|---|---|---|---|
| 1 | Waters: Acquity ® UPLC ®-DAD and SQD | Waters: BEH C18 (1.7 µm, 2.1 * 50 mm) | A: 10 mM $CH_3COONH_4$ in 95% $H_2O$ + 5% $CH_3CN$ B: $CH_3CN$ | From 95% A to 5% A in 1.3 min, held for 0.7 min. | 0.8 / 55 | 2 |
| 2 | Waters: Acquity ® UPLC ®-DAD and SQD | Waters: CSH ™ C18 (1.7 µm, 2.1 × 50 mm) | A: 95% $CH_3COONH_4$ 6.5 mM + 5% $CH_3CN$, B: $CH_3CN$ | From 95% A to 5% A in 4.6 min, held for 0.4 min | 1 / 50 | 5 |
| 3 | Waters: Acquity ® UPLC ®-DAD and SQD | Waters: HSS T3 (1.8 µm, 2.1 * 100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min to 5% A in 0.5 min | 0.8 / 55 | 3.5 |

Melting Points

Values are either peak values or melt ranges, and are obtained with experimental uncertainties that are commonly associated with this analytical method.

For a number of compounds, melting points were determined with a DSC823e (Mettler-Toledo) (a) or a with a Mettler Toledo FP 62 (b) apparatus. Melting points were measured with a temperature gradient of 30° C./minute. Maximum temperature was 400° C.

TABLE 2b

Analytical data - $R_t$ means retention time (in minutes), $[M + H]^+$ means the protonated mass of the compound, method refers to the method used for (LC)MS.

| Co. Nr. | $R_t$ | $[M + H]^+$ | Method | Melting Point |
|---|---|---|---|---|
| 1 | 0.72 | 384 | 1 | n.d. |
| 2 | 0.70 | 391 | 1 | n.d. |
| 3 | 0.71 | 397 | 1 | n.d. |
| 4 | 0.79 | 400 | 1 | n.d. |
| 5 | 1.40 | 439 | 2 | 171.1° C. |
| 6 | 1.76 | 465 | 2 | 163.4° C. |
| 7 | 0.73 | 415 | 1 | n.d. |
| 8 | 0.80 | 402 | 1 | n.d. |
| 9 | 1.29 | 402 | 3 | n.d. |
| 10 | 1.40 | 402 | 3 | n.d. |
| 11 | 1.40 | 402 | 3 | n.d. | n.d. means not determined

Optical Rotations:

Optical rotations were measured on a Perkin-Elmer 341 polarimeter with a sodium lamp and reported as follows: $[\alpha]_\lambda^{t° C.}$ (c g/100 ml, solvent).

TABLE 3

Analytical data - Optical rotation values for enantiomerically pure compounds

| Co. Nr. | $\alpha_D$ (°) | Wavelength (nm) | Concentration w/v % | Solvent | Temp. (° C.) |
|---|---|---|---|---|---|
| 5 | +46.1 | 589 | 0.51 | DMF | 20 |
| 6 | +71.0 | 589 | 0.45 | DMF | 20 |

NMR

For a number of compounds, $^1H$ NMR spectra were recorded on a Bruker DPX-360 operating at 360 MHz or on a Bruker Avance I operating at 500 MHz using CHLOROFORM-d (deuterated chloroform, $CDCl_3$) or DMSO-$d_6$ (deuterated DMSO, dimethyl-d6 sulfoxide) as solvent. Chemical shifts (δ) are reported in parts per million (ppm) relative to tetramethylsilane (TMS), which was used as internal standard.

TABLE 4

$^1$ H NMR results

| Co. No. | $^1$ H NMR result |
|---|---|
| 1 | (360 MHz, DMSO-$d_6$) δ ppm 1.47 (s, 3 H), 4.66 (s, 2 H), 6.82 (br. s., 2 H), 7.19 (dd, J = 12.1, 8.8 Hz, 1 H), 7.66-7.79 (m, 1 H), 7.98 (td, J = 8.8, 2.9 Hz, 1 H), 8.02 (s, 1 H), 8.08 (dd, J = 7.3, 2.6 Hz, 1 H), 8.21 (dd, J = 8.6, 4.6 Hz, 1 H), 8.73 (d, J = 2.9 Hz, 1 H), 10.59 (s, 1 H). |
| 2 | (360 MHz, DMSO-$d_6$) δ ppm 1.47 (s, 3 H), 4.66 (s, 2 H), 6.82 (br. s., 2 H), 7.21 (dd, J = 12.1, 8.8 Hz, 1 H), 7.64-7.82 (m, 1 H), 8.02 (s, 1 H), 8.11 (dd, J = 7.3, 2.6 Hz, 1 H), 8.26 (d, J = 8.1 Hz, 1 H), 8.58 (dd, J = 8.1, 1.5 Hz, 1 H), 9.10-9.29 (m, 1 H), 10.81 (s, 1 H). |
| 3 | (360 MHz, DMSO-$d_6$) δ ppm 1.47 (s, 3 H), 4.02 (s, 3 H), 4.66 (s, 2 H), 6.82 (br. s., 2 H), 7.19 (dd, J = 12.1, 8.8 Hz, 1 H), 7.64-7.78 (m, 1 H), 8.02 (s, 1 H), 8.08 (dd, J = 7.5, 2.7 Hz, 1 H), 8.41 (d, J = 1.5 Hz, 1 H), 8.87 (d, J = 1.5 Hz, 1 H), 10.48 (s, 1 H). |
| 4 | (360 MHz, DMSO-$d_6$) δ ppm 1.47 (s, 3 H), 4.66 (s, 2 H), 6.82 (s, 2 H), 7.20 (dd, J = 12.1, 8.8 Hz, 1 H), 7.69-7.80 (m, 1 H), 8.02 (s, 1 H), 8.08 (dd, J = 7.3, |

TABLE 4-continued

¹ H NMR results

| Co. No. | ¹ H NMR result |
|---|---|
| | 2.6 Hz, 1 H), 8.13 (d, J = 8.1 Hz, 1 H), 8.20 (dd, J = 8.4, 2.6 Hz, 1 H), 8.78 (dd, J = 2.6, 0.7 Hz, 1 H), 10.65 (s, 1 H). |
| 6 | (500 MHz, CHLOROFORM-d) δ ppm 1.58 (s, 3 H), 4.61 (d, J = 13.5 Hz, 1 H), 4.86 (dd, J = 16.5, 8.4 Hz, 2 H), 4.90 (d, J = 14.2 Hz, 1 H), 7.11 (dd, J = 11.6, 8.7 Hz, 1 H), 7.76-7.82 (m, 1 H), 7.86 (s, 1 H), 7.99 (dd, J = 6.9, 2.6 Hz, 1 H), 8.21-8.33 (m, 1 H), 9.00 (d, J = 1.4 Hz, 1 H), 9.48 (s, 1 H). |
| 7 | (360 MHz, DMSO-$d_6$) δ ppm 1.48 (s, 3 H), 4.58-4.74 (m, 2 H), 6.20 (d, J = 51.6 Hz, 2 H), 6.82 (br. s., 2 H), 7.20 (dd, J = 12.1, 8.8 Hz, 1 H), 7.65-7.79 (m, 1 H), 8.02 (s, 1 H), 8.09 (dd, J = 7.3, 2.6 Hz, 1 H), 8.58 (d, J = 1.5 Hz, 1 H), 8.94 (d, J = 1.5 Hz, 1 H), 10.60 (s, 1 H). |
| 8 | (360 MHz, CHLOROFORM-d) δ ppm 1.58 (s, 3 H), 4.58 (d, J = 13.5 Hz, 1 H), 4.93 (d, J = 13.2 Hz, 1 H), 7.51-7.71 (m, 2 H), 7.87 (s, 1 H), 7.98 (ddd, J = 11.5, 6.8, 2.6 Hz, 1 H), 8.31 (dd, J = 8.6, 4.6 Hz, 1 H), 8.45 (d, J = 2.6 Hz, 1 H), 9.83 (s, 1 H). |
| 11 | (360 MHz, DMSO-$d_6$) δ ppm 4.47 (dd, J = 47.2, 9.1 Hz, 1 H), 4.72 (dd, J = 47.6, 9.9 Hz, 1 H), 4.88 (dd, J = 24.5, 13.5 Hz, 2 H), 7.05 (s, 2 H), 7.22 (dd, J = 11.7, 8.8 Hz, 1 H), 7.79 (ddd, J = 8.8, 4.3, 2.7 Hz, 1 H), 7.98 (td, J = 8.8, 2.9 Hz, 1 H), 8.03 (s, 1 H) 8.11 (dd, J = 7.3, 2.6 Hz, 1 H), 8.21 (dd, J = 8.8, 4.8 Hz, 1 H), 8.73 (d, J = 2.9 Hz, 1 H), 10.65 (s, 1 H). |

Pharmacological Examples

The compounds provided in the present invention are inhibitors of the beta-site APP-cleaving enzyme 1 (BACE1). Inhibition of BACE1, an aspartic protease, is believed to be relevant for treatment of Alzheimer's Disease (AD). The production and accumulation of beta-amyloid peptides (Abeta) from the beta-amyloid precursor protein (APP) is believed to play a key role in the onset and progression of AD. Abeta is produced from the amyloid precursor protein (APP) by sequential cleavage at the N- and C-termini of the Abeta domain by beta-secretase and gamma-secretase, respectively.

Compounds of Formula (I) are expected to have their effect substantially at BACE1 by virtue of their ability to inhibit the enzymatic activity. The behaviour of such inhibitors tested using a biochemical Fluorescence Resonance Energy Transfer (FRET) based assay and a cellular αLisa assay in SKNBE2 cells described below and which are suitable for the identification of such compounds, and more particularly the compounds according to Formula (I), are shown in Table 3 and Table 4.

BACE1 Biochemical FRET Based Assay

This assay is a Fluorescence Resonance Energy Transfer Assay (FRET) based assay. The substrate for this assay is an APP derived 13 amino acids peptide that contains the 'Swedish' Lys-Met/Asn-Leu mutation of the amyloid precursor protein (APP) beta-secretase cleavage site. This substrate also contains two fluorophores: (7-methoxycoumarin-4-yl) acetic acid (Mca) is a fluorescent donor with excitation wavelength at 320 nm and emission at 405 nm and 2,4-Dinitrophenyl (Dnp) is a proprietary quencher acceptor. The distance between those two groups has been selected so that upon light excitation, the donor fluorescence energy is significantly quenched by the acceptor, through resonance energy transfer. Upon cleavage by BACE1, the fluorophore Mca is separated from the quenching group Dnp, restoring the full fluorescence yield of the donor. The increase in fluorescence is linearly related to the rate of proteolysis.

Method 1

Briefly in a 384-well format recombinant BACE1 protein in a final concentration of 1 μg/ml is incubated for 120 minutes at room temperature with 10 μm substrate in incubation buffer (40 mM Citrate buffer pH 5.0, 0.04% PEG, 4% DMSO) in the absence or presence of compound. Next the amount of proteolysis is directly measured by fluorescence measurement at T=0 and T=120 (excitation at 320 nm and emission at 405 nm). Results are expressed in RFU (Relative Fluorescence Units), as difference between T120 and T0.

A best-fit curve is fitted by a minimum sum of squares method to the plot of % Controlmin versus compound concentration. From this an $IC_{50}$ value (inhibitory concentration causing 50% inhibition of activity) can be obtained.

LC = Median of the low control values
  = Low control: Reaction without enzyme
HC = Median of the High control values
  = High Control: Reaction with enzyme %Effect = 100 − [(sample-LC/HC-LC) * 100]

%Control = (sample/HC) * 100

%Controlmin = (sample-LC)/(HC-LC) * 100

Method 2

Briefly in a 384-well format recombinant BACE1 protein in a final concentration of 0.04 μg/ml is incubated for 450 minutes at room temperature with 20 μM substrate in incubation buffer (50 mM Citrate buffer pH 5.0, 0.05% PEG) in the presence of compound or DMSO. Next the amount of proteolysis is directly measured by fluorescence measurement (excitation at 320 nm and emission at 405 nm) at different incubation times (0, 30, 60, 90, 120 and 450 min). For every experiment a time curve (every 30 min between 0 min and 120 min) is used to determine the time where we find the lowest basal signal of the high control. The signal at this time (Tx) is used to subtract from the signal at 450 min. Results are expressed in RFU, as difference between T450 and Tx.

A best-fit curve is fitted by a minimum sum of squares method to the plot of % Controlmin versus compound concentration. From this an $IC_{50}$ value (inhibitory concentration causing 50% inhibition of activity) can be obtained.

LC = Median of the low control values

= Low control: Reaction without enzyme

HC = Median of the High control values

= High Control: Reaction with enzyme

%Effect = 100 − [(sample-LC / HC-LC) ∗ 100]

%Control = (sample / HC) ∗ 100

%Controlmin = (sample-LC) / (HC-LC) ∗ 100

The following exemplified compounds were tested essentially as described above and exhibited the following the activity:

TABLE 5

| Co. Nr. | BACE1 Biochemical FRET based assay - Method 1 pIC$_{50}$ | BACE1 Biochemical FRET based assay - Method 2 pIC$_{50}$ |
|---|---|---|
| 1 | 8.28 | 8.37 |
| 2 | 8.75 | 8.75 |
| 3 | 8.69 | 8.69 |
| 4 | 8.76 | 8.75 |
| 5 | n.t. | 8.72 |
| 6 | n.t. | 8.51 |
| 7 | n.t. | 8.52 |
| 8 | n.t. | 8.36 |
| 9 | n.t. | 8.08 |
| 10 | n.t. | 8.39 |
| 11 | n.t. | 6.12 | n.t. means not tested

BACE1 Cellular αLisa Assay in SKNBE2 Cells

In two αLisa assays the levels of Abeta total and Abeta 1-42 produced and secreted into the medium of human neuroblastoma SKNBE2 cells are quantified. The assay is based on the human neuroblastoma SKNBE2 expressing the wild type Amyloid Precursor Protein (hAPP695). The compounds are diluted and added to these cells, incubated for 18 hours and then measurements of Abeta 1-42 and Abeta total are taken. Abeta total and Abeta 1-42 are measured by sandwich αLisa. αLisa is a sandwich assay using biotinylated antibody AbN/25 attached to streptavidin coated beads and antibody Ab4G8 or cAb42/26 conjugated acceptor beads for the detection of Abeta total and Abeta 1-42 respectively. In the presence of Abeta total or Abeta 1-42, the beads come into close proximity. The excitation of the donor beads provokes the release of singlet oxygen molecules that trigger a cascade of energy transfer in the acceptor beads, resulting in light emission. Light emission is measured after 1 hour incubation (excitation at 650 nm and emission at 615 nm).

A best-fit curve is fitted by a minimum sum of squares method to the plot of % Controlmin versus compound concentration. From this an IC$_{50}$ value (inhibitory concentration causing 50% inhibition of activity) can be obtained.

LC = Median of the low control values

= Low control: Reaction without enzyme

HC = Median of the High control values

= High Control: Reaction with enzyme

%Effect = 100 − [(sample-LC / HC-LC) ∗ 100]

%Control = (sample / HC) ∗ 100

%Controlmin = (sample-LC) / (HC-LC) ∗ 100

The following exemplified compounds were tested essentially as described above and exhibited the following the activity:

TABLE 6

| Co. Nr. | Cellular αLisa assay in SKNBE2 cells Abeta 42 pIC$_{50}$ | Cellular αLisa assay in SKNBE2 cells Abetatotal pIC$_{50}$ |
|---|---|---|
| 1 | 8.35 | 8.49 |
| 2 | 8.96 | 8.98 |
| 3 | 8.74 | 8.79 |
| 4 | 8.77 | 8.88 |
| 5 | 8.43 | 8.51 |
| 6 | 8.28 | 8.32 |
| 7 | 8.87 | 8.86 |
| 8 | 8.33 | 8.35 |
| 9 | 7.24 | 7.25 |
| 10 | 7.61 | 7.61 |
| 11 | 5.38 | 5.35 |

BACE2 Biochemical FRET Based Assay

This assay is a Fluorescence Resonance Energy Transfer Assay (FRET) based assay. The substrate for this assay contains the 'Swedish' Lys-Met/Asn-Leu mutation of the amyloid precursor protein (APP) beta-secretase cleavage site. This substrate also contains two fluorophores: (7-methoxycoumarin-4-yl) acetic acid (Mca) is a fluorescent donor with excitation wavelength at 320 nm and emission at 405 nm and 2,4-Dinitrophenyl (Dnp) is a proprietary quencher acceptor. The distance between those two groups has been selected so that upon light excitation, the donor fluorescence energy is significantly quenched by the acceptor, through resonance energy transfer. Upon cleavage by the beta-secretase, the fluorophore Mca is separated from the quenching group Dnp, restoring the full fluorescence yield of the donor. The increase in fluorescence is linearly related to the rate of proteolysis.

Briefly in a 384-well format recombinant BACE2 protein in a final concentration of 0.4 μg/ml is incubated for 450 minutes at room temperature with 10 μM substrate in incubation buffer (50 mM Citrate buffer pH 5.0, 0.05% PEG, no DMSO) in the absence or presence of compound. Next the amount of proteolysis is directly measured by fluorescence measurement at T=0 and T=450 (excitation at 320 nm and emission at 405 nm). Results are expressed in RFU (Relative Fluorescence Units), as difference between T450 and T0.

A best-fit curve is fitted by a minimum sum of squares method to the plot of % Controlmin versus compound concentration. From this an IC$_{50}$ value (inhibitory concentration causing 50% inhibition of activity) can be obtained.

LC = Median of the low control values

= Low control: Reaction without enzyme

HC = Median of the High control values

= High Control: Reaction with enzyme

%Effect = 100 − [(sample-LC/HC-LC)∗100]

%Control = (sample/HC)∗100

%Controlmin = (sample-LC)/(HC-LC)∗100

The following exemplified compounds were tested essentially as described above and exhibited the following activity:

TABLE 7

| Co. Nr. | BACE2 Biochemical FRET based assay $pIC_{50}$ |
|---|---|
| 1 | 8.48 |
| 2 | 8.27 |
| 3 | 7.81 |
| 4 | 8.56 |
| 5 | 8.73 |
| 6 | 7.22 |
| 7 | 7.78 |
| 8 | 8.52 |
| 9 | 8.08 |
| 10 | 8.49 |
| 11 | 6.3 |

Demonstration of In Vivo Efficacy

Aβ lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ lowering agents can be administered in any standard form using any standard method. For example, but not limited to, Aβ lowering agents can be in the form of liquid, tablets or capsules that are taken orally or by injection. Aβ lowering agents can be administered at any dose that is sufficient to significantly reduce levels of Aβ in the blood, blood plasma, serum, cerebrospinal fluid (CSF), or brain.

To determine whether acute administration of an Aβ lowering agent would reduce Aβ levels in vivo, non-transgenic rodents, e.g. mice or rats were used. Animals treated with the Aβ lowering agent were examined and compared to those untreated or treated with vehicle and brain levels of soluble Aβ42, Aβ40, Aβ38, and Aβ37 were quantitated by Meso Scale Discovery's (MSD) electrochemiluminescence detection technology. Treatment periods varied from hours (h) to days and were adjusted based on the results of the Aβ lowering once a time course of onset of effect could be established.

A typical protocol for measuring Aβ lowering in vivo is shown but it is only one of many variations that could be used to optimize the levels of detectable A. For example, Aβ lowering compounds were formulated in 20% of Captisol® (a sulfo-butyl ether of β-cyclodextrin) in water or 20% hydroxypropyl β cyclodextrin. The Aβ lowering agents were administered as a single oral dose or by any acceptable route of administration to overnight fasted animals. After 4 h, the animals were sacrificed and Aβ levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 20800×g for 5 min and supernatants collected. Supernatants were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβ.

To quantify the amount of Aβ42, Aβ40, Aβ38, and Aβ37 in the soluble fraction of the brain homogenates, simultaneous specific detection of Aβ42, Aβ40, Aβ38, and Aβ37 was performed using MSD's electro-chemiluminescence multiplex detection technology. In this assay purified monoclonal antibodies specific for Abeta37 (JRD/Aβ37/3), Abeta38 (J&JPRD/Aβ38/5), Abeta40 (JRF/cAβ40/28), and Abeta42 (JRF/cAβ(342/26) were coated on MSD 4-plex plates. Briefly, the standards (a dilution of synthetic Aβ42, Aβ40, Aβ38, and Aβ37) were prepared in 1.5 ml Eppendorf tube in Ultraculture, with final concentrations ranging from 10000 to 0.3 pg/m. The samples and standards were co-incubated with Sulfo-tag labelled JRF/rAβ/2 antibody to the N-terminus of Aβ as detector antibody. 50 μl of conjugate/sample or conjugate/standards mixtures were then added to the antibody-coated plate. The plate was allowed to incubate overnight at 4° C. in order to allow formation of the antibody-amyloid complex. Following this incubation and subsequent wash steps the assay was finished by adding read buffer according to the manufacturer's instructions (Meso Scale Discovery, Gaithersburg, Md.).

The SULFO-TAG emits light upon electrochemical stimulation initiated at the electrode. MSD Sector instrument SI6000 was used for signal read-out.

In this model a Aβ lowering compared to untreated animals would be advantageous, in particular a Aβ lowering with at least 10%, more in particular a Aβ lowering with at least 20%.

Results

The results are shown in Table 8 (value for untreated animals as control (Ctrl) was set at 100):

TABLE 8

| Co. No. | Aβ40 (% vs Ctrl)_Mean | Aβ42 (% vs Ctrl)_Mean | Dose | Route of administration | Time after administration |
|---|---|---|---|---|---|
| 1 | 47 | 47 | 10 | s.c. | 2 h |
| 1 | 73 | 55 | 10 | s.c. | 4 h |
| 2 | 44 | 44 | 10 | s.c. | 2 h |
| 2 | 61 | 50 | 10 | s.c. | 4 h |
| 8 | 56 | 56 | 10 | s.c. | 2 h |
| 8 | 136 | 105 | 10 | s.c. | 4 h |
| 10 | 95 | 79 | 10 | p.o. | 2 h |
| 10 | 116 | 87 | 10 | p.o. | 4 h | s.c. means subcutaneous;
p.o. means oral

Prophetic Composition Examples

"Active ingredient" as used throughout these examples relates to a final compound of Formula (I), the pharmaceutically acceptable salts thereof, the solvates and the stereochemically isomeric forms thereof Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound of Formula (I)

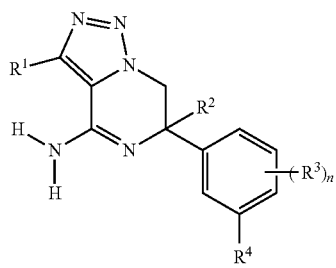

(I)

or a stereoisomeric form thereof, wherein:
$R^1$ is selected from the group consisting of hydrogen; halo; and $C_{1-4}$alkyl;
$R^2$ is selected from the group consisting of $C_{1-4}$alkyl optionally substituted with one or more substituents each independently selected from fluoro and $C_{1-4}$alkyloxy; and
$C_{3-7}$cycloalkyl;
$R^3$ is in each instance an independently selected halo substituent;
n is an integer selected from 1 and 2;
$R^4$ is selected from (a) and (b):

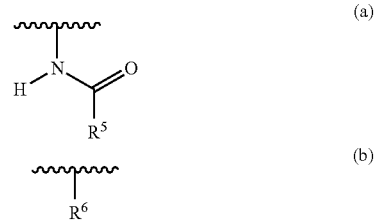

wherein $R^5$ and $R^6$ are each independently selected from the group consisting of aryl and heteroaryl, each of which may be optionally substituted with one or more substituents each independently selected from the group consisting of halo, —CN, $C_{1-4}$alkyl optionally substituted with one or more halo substituents, and $C_{1-4}$alkyloxy optionally substituted with one or more halo substituents;

wherein aryl is phenyl;

wherein heteroaryl is a 5-membered aromatic heterocycle selected from the group consisting of oxazole and pyrazole; or is a 6-membered aromatic heterocycle selected from the group consisting of pyridinyl, pyrimidinyl and pyrazinyl;

or a pharmaceutically acceptable addition salt or a solvate thereof.

2. The compound of claim 1, wherein $R^1$ is hydrogen or halo.

3. The compound of claim 1, wherein $R^2$ is $C_{1-4}$alkyl or $C_{1-4}$alkyl substituted with one or more fluoro substituents.

4. The compound of claim 1, wherein $R^4$ is

wherein $R^5$ is heteroaryl, optionally substituted with one or more substituents each independently selected from the group consisting of halo, —CN, $C_{1-4}$alkyl optionally substituted with one or more halo substituents, and $C_{1-4}$alkyloxy optionally substituted with one or more halo substituents;

wherein heteroaryl is a 5-membered aromatic heterocycle selected from oxazole and pyrazole; or is a 6-membered aromatic heterocycle selected from the group consisting of pyridinyl, pyrimidinyl and pyrazinyl.

5. The compound of claim 1, having the configuration shown in Formula (I')

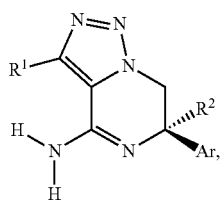

(I')

wherein Ar is

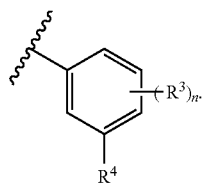

6. A pharmaceutical composition comprising a compound of claim 1 and a pharmaceutically acceptable carrier.

7. A process for preparing a pharmaceutical composition as defined in claim 6, characterized in that the pharmaceutically acceptable carrier is intimately mixed with a therapeutically effective amount of the compound.

8. A method of treating a disorder selected from the group consisting of Alzheimer's Disease (AD), mild cognitive impairment (MCI), memory impairment, senility, dementia, dementia with Lewy bodies, dementia with progressive nuclear palsy, dementia with Cortico-basal degeneration, mixed dementia with Alzheimer's and vascular type, Alzheimer's disorder with difuse Lewy Body disease, amyloid angiopathy, cerebral amyloid angiopathy, multi-infarct dementia, Down's syndrome, dementia associated with Parkinson's disease, dementia of the Alzheimer's type, senile dementia of the Alzheimer's type, vascular dementia, dementia due to HIV disease, dementia due to head trauma, dementia due to Huntington's disease, dementia due to Pick's disease, dementia due to Creutzfeldt-Jakob disease, frontotemporal dementia, dementia pugilistica, dementia associated with beta-amyloid, amyloidosis of the brain and other organs (age and non-age related), Dutch type of hereditary cerebral haemorrhage with amyloidosis, traumatic brain injury (TBI), temporal lobe epilepsy (TLE), hypoxia, ischemia, disruptions in cerebral metabolism, age-related macular degeneration, type 2 diabetes and other metabolic disorders, amyotrophic lateral sclerosis (ALS), multiple sclerosis (MS), arterial thrombosis, autoimmune/inflammatory diseases, breast cancer, myocardial infarction, stroke, hypertension, dermatomyositis, prion disease (Creutzfeld-Jakob disease), gastrointestinal diseases, Glioblastoma multiforme, Graves' Disease, Huntington's Disease, inclusion body myositis (IBM), inflammatory reactions, Kaposi Sarcoma, Kostmann Disease, lupus erythematosus, macrophagic myofasctitis, juvenile idiopathic arthritis, granulomatous arthritis, malignant melanoma, multiple myeloma, rheumatoid arthritis, Sjogren syndrome, SpinoCerebellar Ataxia 1, SpinoCerebellar Ataxia 7, Whippel's Disease and Wilson's Disease, comprising administering to a subject in need thereof, a therapeutically effective amount of a compound as defined in claim 1.

9. A method of treating a disease or condition selected from the group consisting of neurocognitive disorder due to Alzheimer's disease, neurocognitive disorder due to traumatic brain injury, neurocognitive disorder due to Lewy body disease, neurocognitive disorder due to Parkinson's disease, vascular neurocognitive disorder and type 2 diabetes, comprising administering to a subject in need thereof, a therapeutically effective amount of a compound according to claim 1.

10. A method of treating a disorder selected from the group consisting of Alzheimer's Disease (AD), mild cognitive impairment (MCI), memory impairment, senility, dementia, dementia with Lewy bodies, dementia with progressive nuclear palsy, dementia with Cortico-basal degeneration, mixed dementia with Alzheimer's and vascular type, Alzheimer's disorder with difuse Lewy Body disease, amyloid angiopathy, cerebral amyloid angiopathy, multi-infarct dementia, Down's syndrome, dementia associated with Parkinson's disease, dementia of the Alzheimer's type, senile dementia of the Alzheimer's type, vascular dementia, dementia due to HIV disease, dementia due to head trauma, dementia due to Huntington's disease, dementia due to Pick's disease, dementia due to Creutzfeldt-Jakob disease, frontotemporal dementia, dementia pugilistica, dementia associated with beta-amyloid, amyloidosis of the brain and other organs (age and non-age related), Dutch type of hereditary cerebral haemorrhage with amyloidosis, traumatic brain injury (TBI), temporal lobe epilepsy (TLE), hypoxia, ischemia, disruptions in cerebral metabolism, age-related macular degeneration, type 2 diabetes and other metabolic disorders, amyotrophic lateral sclerosis (ALS), multiple sclerosis (MS), arterial thrombosis, autoimmune/inflammatory diseases, breast cancer, myocardial infarction, stroke, hypertension, dermatomyositis, prion disease (Creutzfeld-Jakob disease), gastrointestinal diseases, Glioblastoma multiforme, Graves' Disease, Huntington's Disease, inclusion body myositis (IBM), inflammatory reactions, Kaposi Sarcoma, Kostmann Disease, lupus erythematosus, macrophagic myofasctitis, juvenile idiopathic arthritis, granulomatous arthritis, malignant melanoma, multiple myeloma, rheumatoid arthritis, Sjogren syndrome, SpinoCerebellar Ataxia 1, SpinoCerebellar Ataxia 7, Whippel's Disease and Wilson's Disease, comprising administering to the subject in need thereof, a therapeutically effective amount of a pharmaceutical composition as defined in claim 6.

11. A method of treating a disease or condition selected from the group consisting of neurocognitive disorder due to Alzheimer's disease, neurocognitive disorder due to traumatic brain injury, neurocognitive disorder due to Lewy body disease, neurocognitive disorder due to Parkinson's disease, vascular neurocognitive disorder and type 2 diabetes, comprising administering to a subject in need thereof, a therapeutically effective amount of a pharmaceutical composition according to claim 6.

12. A method of treating a disease or condition selected from the group consisting of mild cognitive impairment (MCI), senility, dementia, dementia with Lewy bodies, Down's syndrome, dementia associated with Parkinson's disease, dementia of the Alzheimer's type, vascular dementia, dementia due to head trauma and dementia associated with beta-amyloid, comprising administering to the subject in need thereof a therapeutically effective amount of a compound as defined in claim 1.

13. A method of treating a disease or condition selected from the group consisting of mild cognitive impairment (MCI), senility, dementia, dementia with Lewy bodies, Down's syndrome, dementia associated with Parkinson's disease, dementia of the Alzheimer's type, vascular dementia, dementia due to head trauma, and dementia associated with beta-amyloid, comprising administering to a subject in need thereof a therapeutically effective amount of a pharmaceutical composition as defined in claim 6.

\* \* \* \* \*